United States Patent
Breadmore et al.

(10) Patent No.: US 9,683,961 B2
(45) Date of Patent: Jun. 20, 2017

(54) ELECTROPHORETIC SEPARATION OF ANALYTES

(71) Applicant: UNIVERSITY OF TASMANIA, Sandy Bay (AU)

(72) Inventors: Michael C. Breadmore, Hobart (AU); Adam J. Gaudry, Hobart (AU); Rosanne M. Guijt, Hobart (AU)

(73) Assignee: University of Tasmania, Sandy Bay (AU)

(*) Notice: Subject to any disclaimer, the term of this patent is extended or adjusted under 35 U.S.C. 154(b) by 169 days.

(21) Appl. No.: 14/417,745

(22) PCT Filed: Aug. 13, 2013

(86) PCT No.: PCT/AU2013/000889
§ 371 (c)(1),
(2) Date: Jan. 27, 2015

(87) PCT Pub. No.: WO2014/026224
PCT Pub. Date: Feb. 20, 2014

(65) Prior Publication Data
US 2015/0192544 A1    Jul. 9, 2015

(30) Foreign Application Priority Data
Aug. 13, 2012 (AU) ................................. 2012903482

(51) Int. Cl.
*G01N 27/453* (2006.01)
*G01N 27/447* (2006.01)

(52) U.S. Cl.
CPC ..... *G01N 27/453* (2013.01); *G01N 27/44713* (2013.01); *G01N 27/44743* (2013.01); *G01N 27/44791* (2013.01)

(58) Field of Classification Search
CPC .......... G01N 27/453; G01N 27/44791; G01N 27/44713; G01N 27/44743
See application file for complete search history.

(56) References Cited

U.S. PATENT DOCUMENTS

| 2002/0112959 A1 | 8/2002 | Xue et al. |
| 2004/0163961 A1 | 8/2004 | Timperman |

(Continued)

OTHER PUBLICATIONS

Blanco, Gustavo A., et al., "Identification of Inorganic Improvised Explosive Devices Using Sequential Injection Capillary Electrophoresis and Contactless Conductivity Detection," Analytical Chemistry vol. 83, No. 23, Oct. 17, 2011, p. 9068-9075.

(Continued)

*Primary Examiner* — Arun S Phasge
(74) *Attorney, Agent, or Firm* — Knobbe, Martens, Olson & Bear, LLP

(57) ABSTRACT

Disclosed are methods and systems for the simultaneous separation and detection of analytes such as anions and cations in a sample using electrophoresis, the method comprising injecting the sample into an electrophoresis system comprising two separation channels through a single sample injection port which is in fluid communication with the two separation channels, separating analytes such as the cations in a first of the two separation channels and simultaneously separation analytes such as the anions in a second of the two separation channels, and detecting the analytes separated in each of the separation channels. Methods and systems are also disclosed that allow the separation and detection of analytes in a sample using electrophoresis in the presence of two or more different electrolytes concurrently, the method comprising providing an electrophoresis system comprising a single sample injection port in fluid communication with two or more separation channels, priming the separation channels with different background electrolytes, injecting (Continued)

the sample through the single sample injection port and into each of the separation channels, applying a voltage potential across each of the separation channels to effect a separation of the analytes in the respective channels during the flow of a different background electrolyte composition through each of the separation channels, and detecting the presence of the analytes in the sample.

21 Claims, 12 Drawing Sheets

(56) References Cited

U.S. PATENT DOCUMENTS

2011/0155575 A1 6/2011 Dorairaj et al.
2011/0220508 A1* 9/2011 Liu .................... C07K 1/26
  204/603

OTHER PUBLICATIONS

Gaudry, Adam J., et al., "On-line simultaneous and rapid separation of anions and cations from a single sample using dual-capillary sequential injection-capillary electrophoresis," Analytica Chimica Acta, vol. 781, Mar. 26, 2013 p. 80-87.

Prest, Jeff E., et al., "Bidirectional isotachophoresis on a planar chip with integrated conductivity detection," The Analyst, vol. 127, No. 11, Oct. 9, 2002, p. 1413-1419.

Reschke, Brent R., et al., "Simultaneous separation and detection of cations and anions on a microfluidic device with suppressed electroosmotic flow and a single injection point," The Analyst, vol. 135, No. 6, Mar. 26, 2010, p. 1351-1359.

Extended European Search Report dated Feb. 26, 2016 for European Application No. 13829717.1.

International Preliminary Report on Patentability dated Dec. 15, 2014, issued in International Application No. PCT/AU2013/000889, filed on Aug. 13, 2013.

* cited by examiner

ELECTROPHORETIC SEPARATION OF ANALYTES

INCORPORATION BY REFERENCE TO RELATED APPLICATIONS

Any and all priority claims identified in the Application Data Sheet, or any correction thereto, are hereby incorporated by reference under 37 CFR 1.57. This application is the national phase under 35 U.S.C. §371 of prior PCT International Application No. PCT/AU2013/000889 which has an International Filing Date of Aug. 13, 2013, which designates the United States of America, and which claims priority to Australian Application No. 2012903482 filed Aug. 13, 2012. Each of the aforementioned applications is incorporated by reference herein in its entirety, and each is hereby expressly made a part of this specification.

FIELD

The present invention relates to methods for the separation and detection of analytes in a sample using electrophoresis, such as capillary electrophoresis or microchip electrophoresis, and to systems for performing such operations. The methods and systems are particularly suited to the simultaneous separation and detection of inorganic anions and cations in a sample.

BACKGROUND

Electrophoresis, encompassing capillary electrophoresis (CE), micellar electrokinetic chromatography (MEKC) and microchip electrophoresis, is a very powerful technique for the analysis of analytes such as ions in a sample. Conventional capillary electrophoresis separates and detects charged ions of one polarity (i.e. anions or cations) through the application of a voltage potential to cause the charged ions to move through a separation capillary at different rates according to their electrophoretic mobility in the presence of a background electrolyte. Such conventional capillary electrophoresis is thus used to detect either the cations present in the sample, or the anions present in the sample. Where the analytes are neutral (uncharged) species, through control of the background electrolyte composition by, for example, the addition of a surfactant, these analytes can also be separated.

It has been recognised that it would be useful for anions and cations present in a sample to be analysed simultaneously. It would similarly be useful to be able to achieve, more generally, the separation and analysis of analytes through multiple separation channels or columns simultaneously.

The benefit of simultaneous analysis of anions and cations is clear; it negates the requirement for two separate analyses. In conventional CE, this is difficult because one of the charged species must migrate against the electroosmotic flow (EOF). It is possible to separate both but only when the EOF is greater than the electrophoretic mobility of the fastest target analyte of opposite polarity to the separation electrode. The practical drawback of this approach is that it is not suitable for the separation of the complete range of inorganic ions. With a cathodic EOF, this approach can separate the full range of cations, but is only suitable for low mobility anions. With an anodic EOF the reverse is true; it can separate the full range of anions but only low mobility cations. The peak capacity of the ions separated in a co-EOF manner is also compromised due to the speed at which they reach the detector.

There have been a small number of publications in recent times that seek to provide a technique for the simultaneous electrophoretic detection of cations and anions. One such technique relies on "dual-opposite end injection" (DOI-CE), in which the positively and negatively charged species are injected from opposite ends of a capillary. During electrophoretic analysis, which occurs under conditions of reduced EOF, analytes migrate from each end of the capillary, in opposite directions towards the detector located near the centre of the capillary. The drawback of this DOI-CE technique is that the separation space is reduced, so there must be precise control of the timing to ensure that anions and cations do not reach the detector at the same time.

Another method of simultaneous anion and cation analysis involves the use of an anionic complexing agent also being the anionic probe. Metal ions are converted to their chelated forms with EDTA or 2,6-pyridinedicarboxylate and separated from other anionic components under anionic separation conditions. Whilst this simplifies the system, this is only applicable to metals that can form an anionic complex and is not suitable for alkali and alkaline earths.

Other techniques considered previously suffer from other drawbacks, such as the requirement to load the sample at multiple points (i.e. multiple sample reservoirs), which then increases the size of the sample required for analysis, and complicates the design of the electrophoresis device and system. Additionally, such techniques rely on the application of a positive potential of differing magnitude at multiple locations in the apparatus, and grounding at two locations, which further complicates the design. Hydrodynamic suppression is achieved through hydrodynamic restrictors of a complicated design which restricts the ability for the apparatus to be created with commercially available equipment, and thus impacts on cost.

It is an object of the invention to provide an alternative technique for the simultaneous separation and detection of cations and anions in a sample. It is desired for the system to produce repeatable results, and to reflect the results that would be expected from two different analyses (for cations and anions) on the sample using conventional techniques. It is also desired for some embodiments to be based on a simple and robust design.

During the course of completing this analysis, it has also been found that the techniques allowing the simultaneous separation and detection of cations and anions can apply more generally to the separation and analysis of analytes (cations, anions or neutral species) through two separation columns via a single injection.

It has also been found that improved electrophoretic methods and systems could be achieved through developing new background electrolyte (or "buffer") delivery options. Thus, according to some embodiments, it is an object to provide a new electrophoresis method and system for the separation of analytes in a sample which has a new degree of flexibility regarding the control of the background electrolyte. This has particular application to techniques that utilise two or more separation channels for the simultaneous separation of ions (e.g. cations in one channel, and anions in the other).

SUMMARY

According to one aspect, there is provided a method for the simultaneous separation and detection of analytes in a sample through two or more separation channels using electrophoresis, the method comprising injecting the sample into an electrophoresis system comprising two or more separation channels through a single sample injection port which is in fluid communication with the two separation channels, separating analytes in each of the separation channels, and detecting the analytes separated in each of the separation channels.

According to one embodiment, the analytes are ions, and in some embodiments the ions comprise anions and cations. Thus, in some embodiments, the method comprises separating the cations in a first of the two separation channels and the anions in a second of the two separation channels. The cations are then detected in the first separation channel and the anions in the second separation channel.

Thus, to summarise the above as it applies to anions and cations as the analytes, according to a second aspect, there is provided a method for the simultaneous separation and detection of anions and cations in a sample using electrophoresis, the method comprising injecting the sample into an electrophoresis system comprising two separation channels through a single sample injection port which is in fluid communication with the two separation channels, separating the cations in a first of the two separation channels and the anions in a second of the two separation channels, and detecting the cations and anions separated in each of the separation channels.

In some embodiments, a positive potential is applied across the first separation channel, and a negative potential is applied across the second separation channel, with a ground electrode located in an interface zone between the entrances to the two separation channels.

Compared to various prior art methods, the present method for simultaneous separation and detection of analytes, such as anions and cations in particular, relies on the supply or injection of a single sample into the system, and the delivery of a portion of that sample into each of the two separation channels. The design established herein allows for such a single sample injection, rather than two sample injections, and does so in an arrangement that is simple and robust. This involves the clever arrangement of electrodes involving the ground electrode being located in the interface zone between the entrances to the two separation channels, and the positioning of a positive electrode for applying a large positive voltage across the first separation channel, and a negative electrode for applying a large negative voltage across the second separation channel. For analytes other than a combination of cations and anions, a different combination of electrodes can be chosen.

In some embodiments, the sample is hydrodynamically loaded into the two separation channels prior to effecting the separation of cations and anions simultaneously in the respective separation channels. This may be achieved through controlled opening and closing of a valve associated with a fluid channel, the fluid channel having an inlet associated with the sample injection port, an interface zone positioned at the entrance to the separation channels, and an outlet downstream of the interface zone. Other techniques can also be used.

The method described above for the simultaneous separation and detection of analytes in a sample through two or more separation channels using electrophoresis may comprise the following specific steps:
  providing an electrophoresis system comprising:
    an injection system comprising a single sample injection port;
    a fluid channel having a fluid channel inlet at one end and a fluid channel outlet at the opposite end, wherein the fluid channel inlet is in fluid communication with the sample injection port, and wherein an interface zone is positioned between the fluid channel inlet and the fluid channel outlet;
    a first separation channel having an entrance positioned in the interface zone of the fluid channel and a first separation channel outlet at the opposite end;
    a second separation channel having an entrance positioned in the interface zone of the fluid channel and a second separation channel outlet at the opposite end;
    a grounded electrode positioned in the fluid channel;
    a first charged electrode positioned to apply a potential across the first separation channel;
    a first detector positioned to detect analytes passing through a detection zone of the first separation channel;
    a second charged electrode positioned to apply a potential across the second separation channel; and
    a second detector positioned to detect analytes passing through a detection zone of the second separation channel;
  priming the two separation channels with background electrolyte, by introducing background electrolyte into the interface zone of the fluid channel and hydrodynamically forcing the background electrolyte into the first and second separation channels;
  loading the sample into the interface zone of the fluid channel by injecting the sample through the single sample injection port to pass into the interface zone of the fluid channel;
  loading the sample into the two separation channels;
  introducing background electrolyte through the fluid channel and into the interface zone of the fluid channel;
  applying a voltage potential across the two separation channels to simultaneously effect a separation of the analytes in the first separation channel and a separation of analytes in the sample in the second separation channel; and
  detecting the presence of the separated analytes through the first detector and the second detector.

In the case of a system for the simultaneous separation and detection of anions and cations in a sample, the analytes comprise anions and cations, the first charged electrode is a positively charged electrode, the second charged electrode is a negatively charged electrode, the first detector detects anions and the second detector detects cations.

Thus, the method for the simultaneous separation and detection of anions and cations in a sample using electrophoresis may comprise the following steps:
  providing a electrophoresis system comprising:
    an injection system comprising a single sample injection port;
    a fluid channel having a fluid channel inlet at one end and a fluid channel outlet at the opposite end, wherein the fluid channel inlet is in fluid communication with the sample injection port, and wherein an interface zone is positioned between the fluid channel inlet and the fluid channel outlet;
    a first separation channel having an entrance positioned in the interface zone of the fluid channel and a first separation channel outlet at the opposite end;
    a second separation channel having an entrance positioned in the interface zone of the fluid channel and a second separation channel outlet at the opposite end;
    a grounded electrode positioned in the fluid channel;
    a positively charged electrode positioned to apply a potential across the first separation channel;

a first detector positioned to detect anions passing through a detection zone of the first separation channel;
a negatively charged electrode positioned to apply a potential across the second separation channel; and
a second detector positioned to detect cations passing through a detection zone of the second separation channel;

priming the two separation channels with background electrolyte, by introducing background electrolyte into the interface zone of the fluid channel and hydrodynamically forcing the background electrolyte into the first and second separation channels;

loading the sample into the interface zone of the fluid channel by injecting the sample through the single sample injection port to pass into the interface zone of the fluid channel;

loading the sample into the two separation channels;

introducing background electrolyte through the fluid channel and into the interface zone of the fluid channel;

applying a voltage potential across the two separation channels to simultaneously effect a separation of the anions present in the sample in the first separation channel and a separation of cations present in the sample in the second separation channel; and detecting the presence of the separated anions through the first detector, and the presence of the separated cations through second detector.

The methods described above may be conducted in a capillary electrophoresis system, on a microchip, or otherwise.

In one embodiment, the method further comprises channeling two different background electrolytes through each of the separation channels during the separation of cations in one separation channel and the anions in the second separation channel. Whilst different background electrolytes may be used for the separation of the cations, as compared to the anions, a multiple electrolyte system with multiple separation channels could alternatively be used for separating the same types of analytes in multiple separation channels. Specifically, the analytes may be neutrally charged species, or ions of one charge only (i.e. either cations or anions, only). The analytes may be a combination of one or more such species (neutral, cations or anions). Multiple separation channels for separating ions of the same polarity with different electrolytes in each may be used to improve the detection and analysis of the ions present in the sample. More generally, the ability to separate and analyse any analytes using different conditions (eg. background electrolyte, column type, polarity of EOF, etc) simultaneously from a single injection of sample would be of great advantage.

Accounting for the multiple electrolyte system, the present application provides a method for the simultaneous separation and detection of anions and cations in a sample using electrophoresis, the method comprising:

providing a electrophoresis system comprising:
an injection system comprising a single sample injection port, a first background electrolyte injection port and a second background electrolyte injection port;
a fluid channel having a fluid channel inlet at one end and a fluid channel outlet at the opposite end, wherein the fluid channel inlet is in fluid communication with the sample injection port, wherein an interface zone is positioned between the fluid channel inlet and the fluid channel outlet; and wherein the first and second background electrolyte injection ports are positioned so that background electrolyte injected through the respective ports will flow concurrently through portions of the fluid channel and pass through portions of the interface zone of the fluid channel;
a first separation channel having an entrance at one end and an outlet at the other end, the entrance of the first separation channel being positioned in a portion of the interface zone of the fluid channel through which the stream of background electrolyte from the first background electrolyte injection port will pass;
a second separation channel having an entrance at one end and an outlet at the other end, the entrance of the second separation channel being positioned in a portion of the interface zone of the fluid channel through which the stream of background electrolyte from the second background electrolyte injection port will pass;
a grounded electrode positioned in the fluid channel;
a positively charged electrode positioned to apply a potential across the first separation channel;
a first detector positioned to detect anions passing through a detection zone of the first separation channel;
a negatively charged electrode positioned to apply a potential across the second separation channel; and
a second detector positioned to detect cations passing through a detection zone of the second separation channel;

priming the two separation channels with background electrolyte, by concurrently introducing background electrolytes from the first and second background electrolyte injection ports into their respective portions of interface zone of the fluid channel, and hydrodynamically forcing background electrolyte from the first background electrolyte port into the first separation channel and background electrolyte from the second background electrolyte port into the second separation channel;

loading the sample into the interface zone of the fluid channel by injecting the sample through the single sample injection port to pass into the interface zone of the fluid channel;

loading the sample into the two separation channels;

concurrently introducing background electrolyte from the first and second background electrolyte injection ports through the fluid channel and into their respective portions of the interface zone of the fluid channel;

applying a voltage potential across the two separation channels to simultaneously effect a separation of the anions present in the sample in the first separation channel, and effect a separation of cations present in the sample in the second separation channel; and detecting the presence of the separated anions through the first detector, and the presence of the separated cations through the second detector.

In addition to the above methods, the present application provides the corresponding systems (or apparatus) for performing electrophoresis.

According to a third aspect, there is provided an electrophoresis system for the simultaneous separation and detection of analytes in a sample, the system comprising:

an injection system comprising a single sample injection port;
a fluid channel having a fluid channel inlet at one end and a fluid channel outlet at the opposite end, wherein the fluid channel inlet is in fluid communication with the sample injection port, and wherein an interface zone is positioned between the fluid channel inlet and the fluid channel outlet;
a background electrolyte reservoir for storing background electrolyte, in fluid communication with the injection system to enable flow of the background electrolyte through the fluid channel;
a first separation channel having an entrance positioned in the interface zone of the fluid channel and a first separation channel outlet at the opposite end;
a second separation channel having an entrance positioned in the interface zone of the fluid channel and a second separation channel outlet at the opposite end;
a grounded electrode positioned in the fluid channel;
a first charged electrode positioned to apply a potential across the first separation channel;
a first detector positioned to detect analytes passing through a detection zone of the first separation channel;
a second charged electrode positioned to apply a potential across the second separation channel;
a second detector positioned to detect analytes passing through a detection zone of the second separation channel; and
a controller for controlling the injection system, flow of background electrolyte through the fluid channel and the application of a voltage across the electrodes.

In the case of a system for the simultaneous separation and detection of anions and cations in a sample, the analytes comprise anions and cations, the first charged electrode is a positively charged electrode, the second charged electrode is a negatively charged electrode, the first detector detects anions and the second detector detects cations.

Thus, in summary, the electrophoresis system for the simultaneous separation and detection of anions and cations in a sample, the system comprises:
  an injection system comprising a single sample injection port;
  a fluid channel having a fluid channel inlet at one end and a fluid channel outlet at the opposite end, wherein the fluid channel inlet is in fluid communication with the sample injection port, and wherein an interface zone is positioned between the fluid channel inlet and the fluid channel outlet;
  a background electrolyte reservoir for storing background electrolyte, in fluid communication with the injection system to enable flow of the background electrolyte through the fluid channel;
  a first separation channel having an entrance positioned in the interface zone of the fluid channel and a first separation channel outlet at the opposite end;
  a second separation channel having an entrance positioned in the interface zone of the fluid channel and a second separation channel outlet at the opposite end;
  a grounded electrode positioned in the fluid channel;
  a positively charged electrode positioned to apply a potential across the first separation channel;
  a first detector positioned to detect anions passing through a detection zone of the first separation channel;
  a negatively charged electrode positioned to apply a potential across the second separation channel;
  a second detector positioned to detect cations passing through a detection zone of the second separation channel; and
  a controller for controlling the injection system, flow of background electrolyte through the fluid channel and the application of a voltage across the electrodes.

Further aspects described herein include methods and systems for the separation and detection of analytes (such as anions and cations) in a sample that make use of two or more different electrolyte compositions for separating the analytes concurrently.

Thus, according to a fourth aspect, there is provided a method for the separation and detection of analytes in a sample using electrophoresis in the presence of two or more different electrolytes concurrently, the method comprising providing an electrophoresis system comprising a single sample injection port in fluid communication with two or more separation channels, priming the separation channels with different background electrolytes, injecting the sample through the single sample injection port and into each of the separation channels, applying a voltage potential across each of the separation channels to effect a separation of the analytes in the respective channels during the flow of a different background electrolyte through each of the separation channels, and detecting the presence of the analytes in the sample.

The expression "priming the separation channels with different background electrolytes" refers to "priming each separation channel with a background electrolyte of a different composition to the background electrolyte primed into the other separation channel". Different composition refers to a different chemical composition, and may, for example, be a difference in the concentration and/or identity of the chemical components in the background electrolyte. This may also be referred to as a buffer.

This system provides the capability to concurrently analyse samples using different background electrolytes, which can be very useful when different background electrolytes may be suited for the separation of different analytes, such as ions, present in the sample.

The method the simultaneous separation and detection of analytes in a sample through two or more separation channels using electrophoresis may comprise:
  providing a electrophoresis system comprising:
    an injection system comprising a single sample injection port, a first background electrolyte injection port and a second background electrolyte injection port;
    a fluid channel having a fluid channel inlet at one end and a fluid channel outlet at the opposite end, wherein the fluid channel inlet is in fluid communication with the sample injection port, wherein an interface zone is positioned between the fluid channel inlet and the fluid channel outlet; and wherein the first and second background electrolyte injection ports are positioned so that background electrolyte injected through the respective ports will flow concurrently through portions of the fluid channel and pass through portions of the interface zone of the fluid channel;
    a first separation channel having an entrance at one end and an outlet at the other end, the entrance of the first separation channel being positioned in a portion of the interface zone of the fluid channel through which the stream of background electrolyte from the first background electrolyte injection port will pass;
    a second separation channel having an entrance at one end and an outlet at the other end, the entrance of the second separation channel being positioned in a portion of the interface zone of the fluid channel through which the stream of background electrolyte from the second background electrolyte injection port will pass;
    a grounded electrode positioned in the fluid channel;

a charged electrode positioned to apply a potential across the first separation channel;

a first detector positioned to detect analytes passing through a detection zone of the first separation channel;

a charged electrode positioned to apply a potential across the second separation channel; and a second detector positioned to detect analytes passing through a detection zone of the second separation channel;

priming the two separation channels with background electrolyte, by concurrently introducing background electrolytes from the first and second background electrolyte injection ports into their respective portions of interface zone of the fluid channel, and hydrodynamically forcing background electrolyte from the first background electrolyte port into the first separation channel and background electrolyte from the second background electrolyte port into the second separation channel;

loading the sample into the interface zone of the fluid channel by injecting the sample through the single sample injection port to pass into the interface zone of the fluid channel;

loading the sample into the two separation channels;

concurrently introducing background electrolyte from the first and second background electrolyte injection ports through the fluid channel and into their respective portions of the interface zone of the fluid channel;

applying a voltage potential across the two separation channels to simultaneously effect a separation of the analytes in the first separation channel, and effect a separation of analytes in the second separation channel; and detecting the presence of the separated analytes through the first detector and the second detector.

In the case of samples comprising anions and cations as the analyte, the first charged electrode may be a positively charged electrode, the second charged electrode may be a negatively charged electrode, the first detector detects anions, and the second detector detects cations.

According to a fifth aspect, there is also provided an electrophoresis system for the simultaneous separation and detection of analytes in a sample, the system comprising:

a first background electrolyte reservoir for storing a first background electrolyte and a second background electrolyte reservoir for storing a second background electrolyte;

an injection system comprising a single sample injection port, a first background electrolyte injection port and a second background electrolyte injection port;

a fluid channel having a fluid channel inlet at one end and a fluid channel outlet at the opposite end, wherein the fluid channel inlet is in fluid communication with the sample injection port, wherein an interface zone of the fluid channel is positioned between the fluid channel inlet and the fluid channel outlet; and wherein the first and second background electrolyte injection ports are positioned so that background electrolyte injected concurrently through the respective ports can flow concurrently through portions of the fluid channel to pass through portions of the interface zone of the fluid channel;

a first separation channel having an entrance at one end and an outlet at the other end, the entrance of the first separation channel being positioned in a portion of the interface zone of the fluid channel through which the stream of background electrolyte from the first background electrolyte injection port will pass;

a second separation channel having an entrance at one end and an outlet at the other end, the entrance of the second separation channel being positioned in a portion of the interface zone of the fluid channel through which the stream of background electrolyte from the second background electrolyte injection port will pass;

a grounded electrode positioned in the fluid channel;

a first charged electrode positioned to apply a potential across the first separation channel;

a first detector positioned to detect analytes passing through a detection zone of the first separation channel;

a second charged electrode positioned to apply a potential across the second separation channel;

a second detector positioned to detect analytes passing through a detection zone of the second separation channel; and a controller for controlling the injection system, flow of the first and second background electrolytes through the fluid channel and the application of a voltage across the electrodes.

In the case of a system for the simultaneous separation and detection of anions and cations in a sample, the analytes comprise anions and cations, the first charged electrode is a positively charged electrode, the second charged electrode is a negatively charged electrode, the first detector detects anions and the second detector detects cations.

BRIEF DESCRIPTION OF THE DRAWINGS

FIGS. 8A to 8E show the following stages: 8A—priming; 8B—sample loading; 8C—hydrodynamic injection; 8D—buffer flushing; and 8E—separation. Some apparatus components illustrated in FIG. 7 are absent from FIGS. 8A to 8E, to simplify the figures.

DETAILED DESCRIPTION

As described above, the present application relates to methods and systems for the simultaneous separation and detection of analytes, such as anions and cations, in a sample using electrophoresis. These methods and systems are described in detail below primarily using the example of cations and anions as the analytes. However, any such references to anions and cations should be read as applying to the separation of analytes more generally, with any necessary modifications as required.

In general terms, one method comprises injecting the sample into an electrophoresis system comprising two separation channels through a single sample injection port in fluid communication with the two separation channels, separating the cations in one separation channel and the anions in a second separation channel, and detecting the cations and anions separated in each of the separation channels.

It is noted that, whilst one of the separation columns in some embodiments is intended to separate cations and the other anions, when a combination of two different background electrolytes are used, the two separation columns may be used to separate ions of the same charge (i.e. positive (cations) or negative (anions)), or to separate neutrally charged species. In such embodiments, the background electrolyte composition can be varied between the two columns, to allow for simultaneous separations to be carried out on the one sample using these different conditions, to as quickly as possible (and within the same device) obtain a better analysis of the analytes, such as ion components, in the sample.

The term "separation channel" encompasses separation capillaries, and other channel arrangements such as micromachined channels in microchips, through which separation of analytes or ions can be effected. Such channels are typically much narrower in diameter than the main fluid channel through which the sample and background electrolyte is delivered into the separation channels. In the following, where references are made to capillary electrophoresis, it will be understood that the same arrangement may be applied to other forms of electrophoresis such as microchip electrophoresis and MEKC, and therefore such references are not limiting in this regard.

Figure 1:
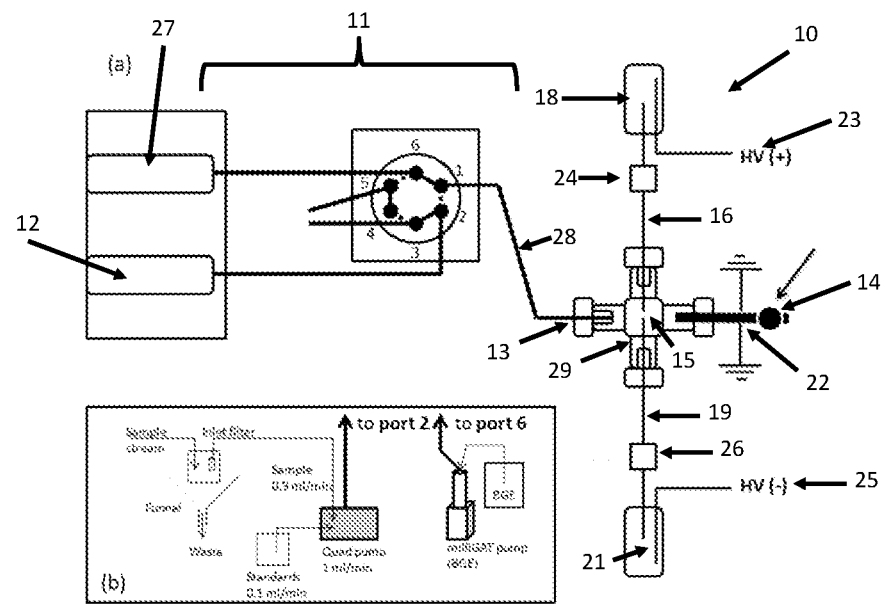
FIG. 1(a) is a schematic diagram of the SI-CE system of one embodiment of the invention. HV: High Voltage electrode, $C^4D$: capacitively-coupled contactless conductivity detector.
FIG. 1(b) is a schematic diagram of the SI-CE system adapted for on-line sampling.

FIG. 1 illustrates schematically one possible arrangement for the apparatus, device or system of one embodiment of the invention. Referring to FIG. 1, and as outlined above, where the analytes are cations and anions, the specific apparatus and stages used in the method may involve the following:

providing a electrophoresis system 10 comprising:
- an injection system 11 comprising a single sample injection port (not shown in detail—see numeral 12 generally);
- a fluid channel having a fluid channel inlet 13 at one end and a fluid channel outlet 14 at the opposite end, wherein the fluid channel inlet is in fluid communication with the sample injection port, and wherein an interface zone 15 is positioned between the fluid channel inlet and the fluid channel outlet;
- a first separation channel 16 having an entrance 17 positioned in the interface zone 15 of the fluid channel and a first separation channel outlet 18 at the opposite end;
- a second separation channel 19 having an entrance 20 positioned in the interface zone 15 of the fluid channel and a second separation channel 21 outlet at the opposite end;
- a grounded electrode 22 (represented by the thick black line) positioned in the fluid channel;
- a positively charged electrode 23 positioned to apply a potential across the first separation channel 16;
- a first detector 24 positioned to detect anions passing through a detection zone of the first separation channel;
- a negatively charged electrode 25 positioned to apply a potential across the second separation channel 19; and
- a second detector 26 positioned to detect cations passing through a detection zone of the second separation channel;

priming the two separation channels with background electrolyte (pumped through a background electrolyte pump 27), by introducing background electrolyte into the interface zone 15 of the fluid channel via a fluid passageway 28 and the fluid channel inlet 13, and hydrodynamically forcing the background electrolyte into the first and second separation channels 16,19;

loading the sample into the interface zone 15 of the fluid channel by injecting the sample through the single sample injection port 12 to pass into the interface zone 15 of the fluid channel (via the fluid passageway 28 and the fluid channel inlet 13);

loading the sample into the two separation channels 16,19;

introducing background electrolyte through the fluid channel and into the interface zone 15 of the fluid channel;

applying a voltage potential across the two separation channels 16,19 to simultaneously effect a separation of the anions present in the sample in the first separation channel 16 and a separation of cations present in the sample in the second separation channel 19; and detecting the presence of the separated anions through the first detector 24, and the presence of the separated cations through the second detector 26.

The injection system comprises a single sample injection port. The sample injection port is a port through which the sample is delivered into the apparatus by the operator of the apparatus, and excludes systems in which the operator must deliver the sample at two locations.

The injection system typically will further comprise at least one background electrolyte injection port. In the following paragraphs we describe one embodiment where a single background electrolyte is utilised. Further below a second embodiment based on multiple background electrolytes will be described.

The sample injection system may further comprise an injector valve which can be operated to control opening of the fluid channel to either the sample injection port, to enable sample entry into the fluid channel, or to the background electrolyte. In the embodiment shown in FIG. 1, the injector (or injection) valve 27 includes one setting, marked 2, controlling opening of the fluid channel to the sample injection port, and one setting, marked 6, controlling opening of the fluid channel to the background electrolyte. The background electrolyte may be pumped through operation of a pump, or any other fluid flow generator, into the fluid channel when the injector valve is positioned to allow the fluid to flow from the background electrolyte reservoir. Consequently, the system may comprise a fluid flow generator for generating a flow of background electrolyte through the fluid channel.

The fluid channel comprises an inlet at the injection system end of the fluid channel, and an outlet. An interface zone of the fluid channel is positioned between the two ends. The fluid channel may be provided by a channel that extends between and includes the two opposite arms of a cross-shaped (X-shaped) connection. In the embodiment shown in FIG. 1, the cross-shaped connection is marked 29. The separation channels in this case project into an interface zone of the fluid channel at the cross-junction. The tips of the two separation capillaries (separation channels) may protrude into the interface zone of the fluid channel. The tips of the separation capillaries (i.e. the entrances or openings to the separation channels) are spaced an equal distance from the centre axis of the fluid channel.

A ground electrode is provided in the interface zone of the fluid channel. The ground electrode may be an elongate, hollow electrode, such as a cylindrical electrode. This is shown in the embodiment of FIG. 1 as a dark line 22 extending into one arm of the cross-shaped connection 29. The cylindrical ground electrode may extend axially from the outlet end of the fluid channel and into the interface zone of the fluid channel. This grounded electrode design enables the sample to be introduced into the separation channel over a much shorter time period compared to the prior art. The time is about one second, compared to the prior art 20-30 second time period. The cylindrical wall of the ground electrode may define a portion of the fluid channel, and the outlet of the fluid channel may be via the centre of the cylindrical ground electrode.

The internal diameter of the fluid channel may be in the region of about 50 to 1000 µm (i.e. up to 1 mm in diameter), such as between 50 and 800 µm, 100 and 800 µm, or between 300 and 800 µm. The internal diameter of the fluid channel used in the Examples was 500 µm.

The background electrolyte may be stored in a background electrolyte reservoir, which is in fluid communication with the injection system to enable it to flow through the fluid channel. During the time period of the separation, the background electrolyte flow rate may be in the region of about 10 to 1000 µL·min$^{-1}$ and typically it will be in the region of about 10 to 200 µL/min.

The background electrolyte may be of any suitable composition as known in the art. The background electrolyte may comprise one or more buffers, and any other typical electrolyte components. The background electrolyte may consist of buffers, and may therefore be referred to as a buffer. The background electrolyte may comprise a polymer component, such as a polyelectrolyte, such as polyethyleneimine (PEI). In embodiments where the analyte is a neutrally charged species, the background electrolyte may comprise a charged surfactant. An example of a charged surfactant is sodium dodecyl sulphate. The charged surfactant interacts with neutrally charged analytes, and the analytes are separated in the separation channel on the basis of the extent to which they interact with the charged surfactant. This may be used in the case of MEKC.

The separation channels, or separation capillaries, may be of the same constitution, or may be different. The separation capillaries may be fused silica capillaries. Each separation capillary may be coated or uncoated. Each capillary may have an internal diameter of about 10 to 100 µm, such as 10 to 75 µm.

The tips of the separation capillaries (i.e. the entrances to the separation channels) are suitably positioned an equal distance from the ground electrode. This ensures that the electromagnetic field applied will be even as between the two separation capillaries.

The distance between the entrances to the first and second separation channels is preferably at least 50 µm. The entrances may be up to 500 µm apart.

The capillary internal diameter influences the minimum separation distance required. The separation distance should be a minimum of 1 times, preferably 2 times, or up to 20 times the capillary internal diameter. A typical separation distance is about 7.5 times the internal diameter—or between about 5 and 10 times the internal diameter.

The length of each separation capillary may be about 15 cm or longer, and up to 100 cm, although shorter capillary lengths of between 15 cm and 50 cm are preferred, for shorter separation times. This length refers to the total column length. It is noted that the detection zone will typically be spaced apart from the exit end of the capillary, for example, about 10 cm from the exit or outlet end of the capillary, so the effective length is shorter by a length corresponding to the detection zone location. The detector associated with each capillary may be positioned at any suitable location along the capillary length, and in some embodiments, is located around 5-15 cm from the inlet to the capillary.

Each capillary comprises a detection zone. This is spaced apart from the entrance to the capillary a distance sufficient for the separation to have taken place.

Each detector may be any suitable form of detector for detecting the presence (and relative amount) of the analytes. In some embodiments the detector is used for detecting inorganic ions. Examples include optical detectors, such as photometric detectors, and contactless conductivity detectors, including capacitively-coupled contactless conductivity detectors ($C^4D$). Other types of detectors known in the art for detecting analytes in electrophoresis (such as MEKC) can be used. The signal produced by the detector is suitably converted by a controller into a visual image to facilitate recording and analysis of the signal. The detector zone of the separation channel (separation capillary) is suitably positioned a distance between 5 cm and 15 cm from the outlet of the separation channel, such as at a distance of about 10 cm from the outlet of the separation channel. The detector is aligned with the detection zone.

The methods/systems enable the detection of the inorganic ions of interest at concentrations of 10 ppm (parts per million) or even less. Detection can be achieved down to 1 ppb (parts per billion). The detection limits depend in part on the detectors used, but with $C^4D$ detectors these levels are achievable. The system enables the screening within a 1 minute time-frame.

In the case of the analytes being inorganic anions, the inorganic anions that can be separated by the method/system include chloride, sulfate, thiocyanate, fluoride, phosphate, carbonate, nitrate, perchlorate, azide, chlorate and $CH_3SO_3^-$ ions. In the case of analytes which are inorganic cations, inorganic cations that can be separated in the method/system include calcium, potassium, sodium, $NH_4^+$ and magnesium. A sample containing a combination of cations and anions selected from the above can be analysed in the present method/system to enable the simultaneous separation and detection of the cations and anions.

In the case of other analytes, these may include proteins, DNA, aptmers, organic compounds such as hydrocarbons, small organic molecules, pharmaceuticals, biologically active molecules, and so forth.

The charged electrode for the first separation channel may be a positively charged electrode. The charged electrode associated with the first separation channel (for separating anions in some embodiments) is positioned to apply a voltage potential across the first separation channel (which may be in the form of a capillary), with the ground electrode in the interface zone. The charged electrode may be located towards or at the outlet end of the first separation channel (or capillary). The electrode is typically a high voltage electrode.

The charged electrode for the second separation channel may be a negatively charged electrode. The charged electrode associated with the second separation channel (for separating cations in some embodiments) is positioned to apply a voltage potential across the second separation channel (which may be in the form of a capillary), with the ground electrode in the interface zone. The charged electrode may be located towards or at the outlet end of the second separation channel (or capillary). The electrode is typically a high voltage electrode.

A high voltage is applied across the separation channels or capillaries (longitudinally) during the separation stage during flow of background electrolyte through the fluid channel. Typical voltages applied during this step are up to 40 kV, such as about 30 kV or 25 kV (positive or negative). The voltage may be modulated over this time period—for example, the voltage may increase at a fixed or variable rate up to the maximum voltage being applied, or the voltage may be increased step-wise. When a voltage potential is applied by the positive and negative electrodes, it is generally of the same magnitude, but of the opposite potential.

After loading of the sample into the interface zone of the fluid channel by injecting the sample through the single sample injection port to pass into the interface zone of the fluid channel, the sample is loaded into the separation channels. This may be achieved hydrodynamically (through techniques to be described in further detail below), or electrokinetically, through the application of a voltage potential.

If sample loading is conducted electrokinetically, a small voltage potential is applied across the two separation channels (capillaries) for a short period during the final stage of sample injection (loading), to cause ions present in the sample to pass along the respective capillaries. This enables a minimum "injection" of ions into the capillary to provide sufficient sensitivity. Suitable voltage and time periods for this step are about 1 kV for about 1 second (negative for the negative electrode, and positive for the positive electrode), with variation possible between −0.2 kV to 5 kV for between 0.2 and 3 seconds (with an increased voltage corresponding to a shorter time, and vice versa).

In some embodiments, the sample is hydrodynamically loaded into the two separation channels prior to effecting the separation of cations and anions simultaneously in the respective separation channels. According to some embodiments, the fluid channel comprises a valve for controlling the opening and closing of the fluid channel outlet. The hydrodynamic loading may be achieved through controlled opening and closing of this valve. For example, to load the sample into the two separation channels hydrodynamically, the sample is loaded into the interface zone, the fluid channel outlet valve is closed, and then the sample is injected through the sample injection port with the valve still closed to hydrodynamically force the sample into the two separation channels. This clever design enables simple and reliable hydrodynamic loading of the sample, and background electrolytes, into the separation capillaries.

With a valve present to control opening and closing of the fluid channel outlet, the following steps (one or all) can be utilised in the method:

during priming, the fluid channel outlet is closed to hydrodynamically force the background electrolyte into the first and second separation channels;

loading of sample into interface zone is performed with the fluid channel outlet open;

loading the sample into the separation channels is achieved by closing the fluid channel outlet and injecting the sample through the sample injection port to hydrodynamically force the sample into the two separation channels;

background electrolyte is introduced through the fluid channel and into the interface zone of the fluid channel with the fluid channel outlet open; and the step of applying a voltage potential across the separation channels to effect separation of the analytes is operated during flow of background electrolyte through the fluid channel; and/or the voltage potential is applied across the two separation channels with the fluid channel outlet open.

According to some embodiments, the step of loading the sample through injecting the sample into the single sample injection port to pass into the interface zone of the fluid channel is followed by the separate introduction of background electrolyte into the interface zone. This enables a "plug" of the sample to be loaded into the separation channels.

Two Electrolyte System

As described above, the present application also relates to a method and system for the separation and detection of analytes in a sample using electrophoresis in the presence of two or more different electrolytes concurrently. In general terms, the method comprises providing an electrophoresis system comprising a single sample injection port in fluid communication with two or more separation channels, priming the separation channels with different background electrolytes, injecting the sample through the single sample injection port and into each of the separation channels, applying a voltage potential across each of the separation channels to effect a separation of the analytes in the respective channels during the flow of a different background electrolyte through each of the separation channels, and detecting the presence of the analytes in the sample.

As noted above, this system provides the capability to concurrently analyse samples using different background electrolytes, which can be very useful when different background electrolytes may be suited for the separation of different analytes present in the sample. The background electrolytes differ in their composition, concentration, pH or otherwise. In one embodiment, one of the separation channels may be for the separation and detection of cations, and the second may be for the separation and detection of anions. According to some embodiments, the separation channels include a separation channel for separating cations and a separation channel for separating anions. Any additional separation channels may be for the separation of cations or anions. According to other embodiments, the separation channels are for separating analytes of the same charge (i.e. positive or negative or neutral).

As outlined above in the context of anions and cations as the analytes, the specific apparatus and stages used in the method may involve the following:

providing a electrophoresis system comprising:
an injection system comprising a single sample injection port (in the form of channel 30), a first background electrolyte injection port (in the form of channel 31) and a second background electrolyte injection port (in the form of channel 32);
a fluid channel 33 having a fluid channel inlet 34 at one end and a fluid channel outlet 35 at the opposite end, wherein the fluid channel inlet 34 is in fluid communication with the sample injection port 30, wherein an interface zone 35 is positioned between the fluid channel inlet and the fluid channel outlet; and wherein the first and second background electrolyte injection ports 31, 32 are positioned so that background electrolyte injected through the respective ports will flow concurrently through portions of the fluid channel and pass through portions of the interface zone of the fluid channel (see the shaded sections, with dark grey shading 36 representing the first background electrolyte and white 37 representing the second background electrolyte);
a first separation channel 38 having an entrance at one end 39 and an outlet 40 at the other end, the entrance of the first separation channel being positioned in a portion of the interface zone 35 of the fluid channel through which the stream of background electrolyte from the first background electrolyte injection port will pass;
a second separation channel 41 having an entrance 42 at one end and an outlet 43 at the other end, the entrance of the second separation channel 42 being positioned in a portion of the interface zone 35 of the fluid channel through which the stream of background electrolyte from the second background electrolyte injection port will pass;
a grounded electrode (not shown in detail, but in the region indicated by 44) positioned in the fluid channel 33;
a positively charged electrode 45 positioned to apply a potential across the first separation channel;
a first detector 46 positioned to detect anions passing through a detection zone of the first separation channel;
a negatively charged electrode 47 positioned to apply a potential across the second separation channel; and
a second detector 48 positioned to detect cations passing through a detection zone of the second separation channel;
priming the two separation channels with background electrolyte, by concurrently introducing background electrolytes from the first and second background electrolyte injection ports into their respective portions of interface zone of the fluid channel, and hydrodynamically forcing background electrolyte from the first background electrolyte port into the first separation channel and background electrolyte from the second background electrolyte port into the second separation channel;
loading the sample into the interface zone of the fluid channel by injecting the sample through the single sample injection port to pass into the interface zone of the fluid channel;
loading the sample (from the interface zone of the fluid channel) into the two separation channels;
concurrently introducing background electrolyte from the first and second background electrolyte injection ports through the fluid channel and into their respective portions of the interface zone of the fluid channel;
applying a voltage potential across the two separation channels to simultaneously effect a separation of the anions present in the sample in the first separation channel, and effect a separation of cations present in the sample in the second separation channel; and
detecting the presence of the separated anions through the first detector, and the presence of the separated cations through the second detector.

The device features for this two-electrolyte invention are generally the same as for arrangement as described above, other than for the provision of two background electrolyte injection ports (and two background electrolyte reservoirs) within the injection system. Whilst that is the case, this embodiment is particularly suited to microchip electrophoresis. Accordingly, in the following, we have described the two electrolyte system invention in further detail in the context of microchip electrophoresis.

The microchip design for a two-electrolyte system may comprise a microchip containing:

the fluid channel 33 described above (herein referred to as the "main fluid channel" or "central fluid channel"), three channels 30, 31, 32 leading to the inlet end of the main fluid channel which are in fluid communication with a sample injection port and two background electrolyte injection ports, and two separation channels 38, 39 that branch laterally outwardly (in a perpendicular direction) from the main fluid channel.

Fluid outlets are provided at the outlet end of the main fluid channel 35, and at the outlet ends of the separation channels 40,43, for draining liquids away from the microchip.

This microchip design could also be used for the single electrolyte system embodiments described above, either with all three channels 30, 31, 32, or just two fluid channels, one for the sample and the second for the background electrolyte.

Figure 7:
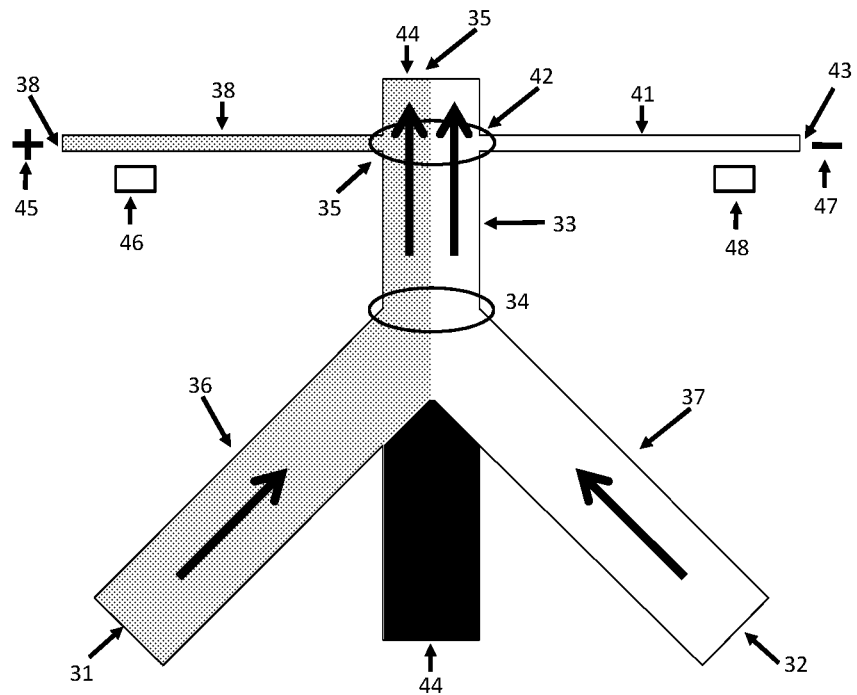
FIG. 7 is a schematic diagram of a microchip electrophoresis system for delivering different background electrolytes to each of two separation channels in accordance with one embodiment of the invention.

The three channels that lead to the inlet end of the fluid channel are arranged so that when respective background electrolytes are injected into their ports and through the injection channels towards the main fluid channel, the background electrolytes will flow concurrently in their own streams, and without mixing, through the fluid channel. In the arrangement shown in FIG. 7, two separate streams of background electrolytes flow in parallel through the fluid channel and through portions of the interface zone. Those portions are the left side and the right side of the interface zone, as shown in FIG. 7. Since the separation channel entrances are located in a portion of the interface zone (one side, as shown in FIG. 7) through which only one of the background electrolyte compositions pass, just the background electrolyte that passes through that portion of the interface zone will flow (when subjected to the required hydrodynamic force) into the subject separation channel. In other embodiments, such as that shown in FIG. 9, the sections of the interface zone through which the different background electrolytes flow constitute longitudinal sections of the fluid channel.

With this arrangement, it becomes possible to control different chemistries for the background electrolyte in each separation channel.

As in the first arrangement described above in the context of CE, the fluid channel outlet preferably comprises a valve for the controlled opening and closing of the fluid channel outlet.

Figure 8A:
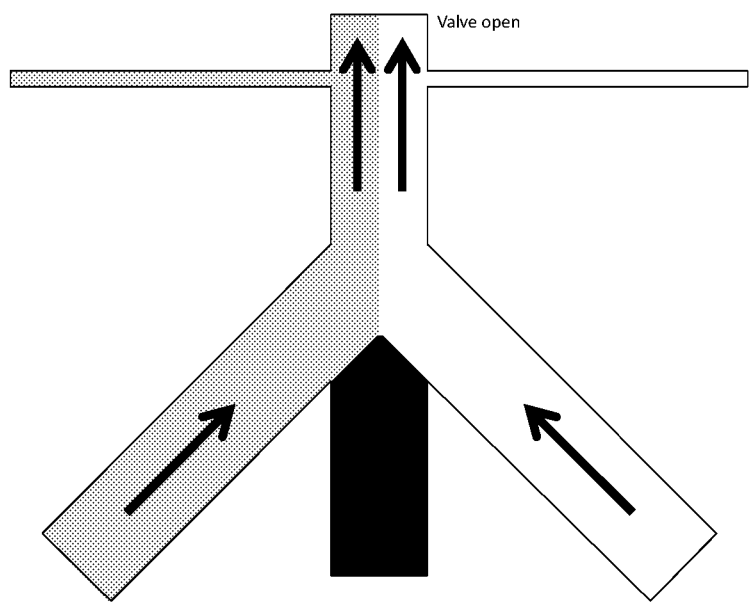
FIGS. 8A to 8E are a schematic diagrams showing the various stages of the process for separating and analyzing ions through microchip electrophoresis using the arrangement illustrated in FIG. 7, utilizing delivering different background electrolytes for the separations conducted in each of the two separation channels.
Figure 8B:
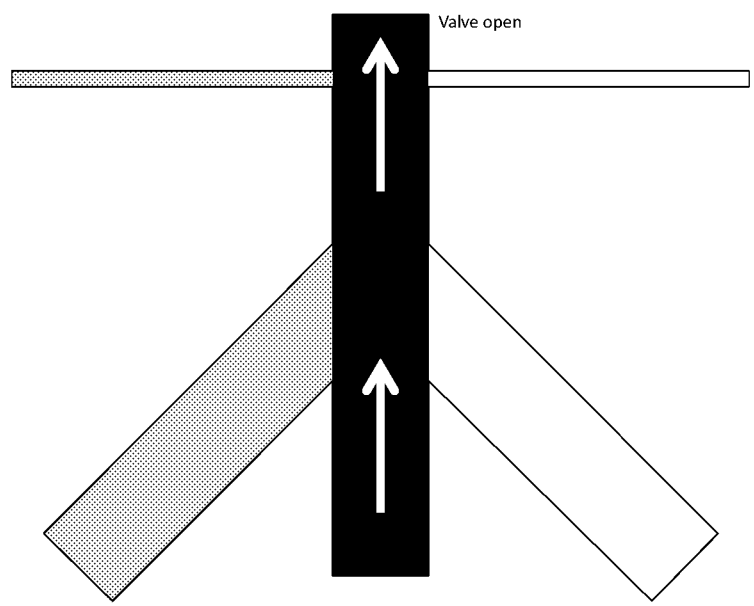
Figure 8C:
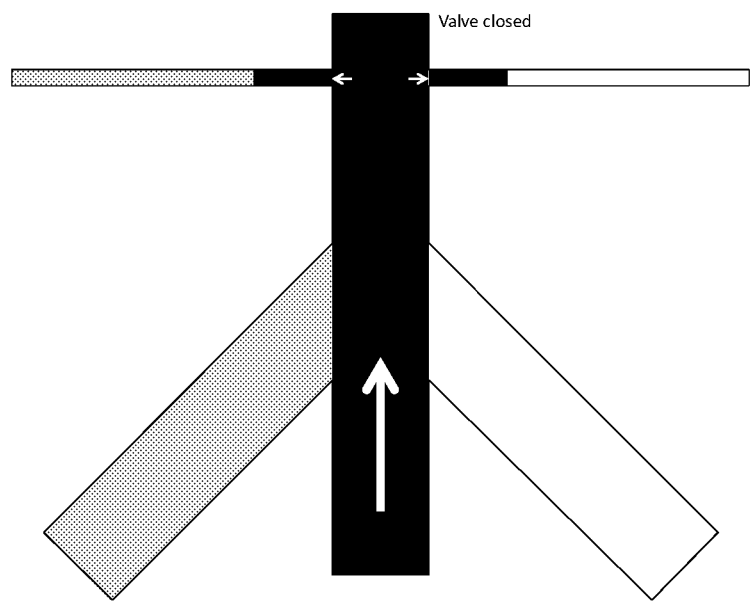
Figure 8D:
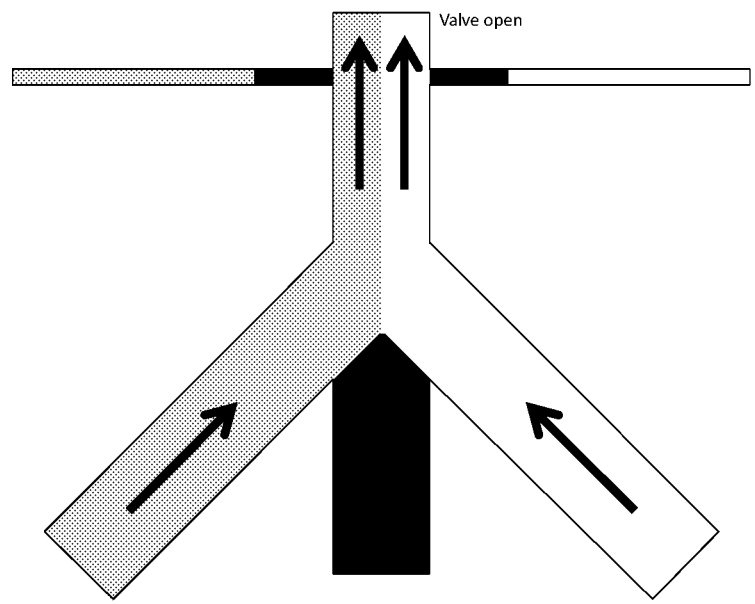
Figure 8E:
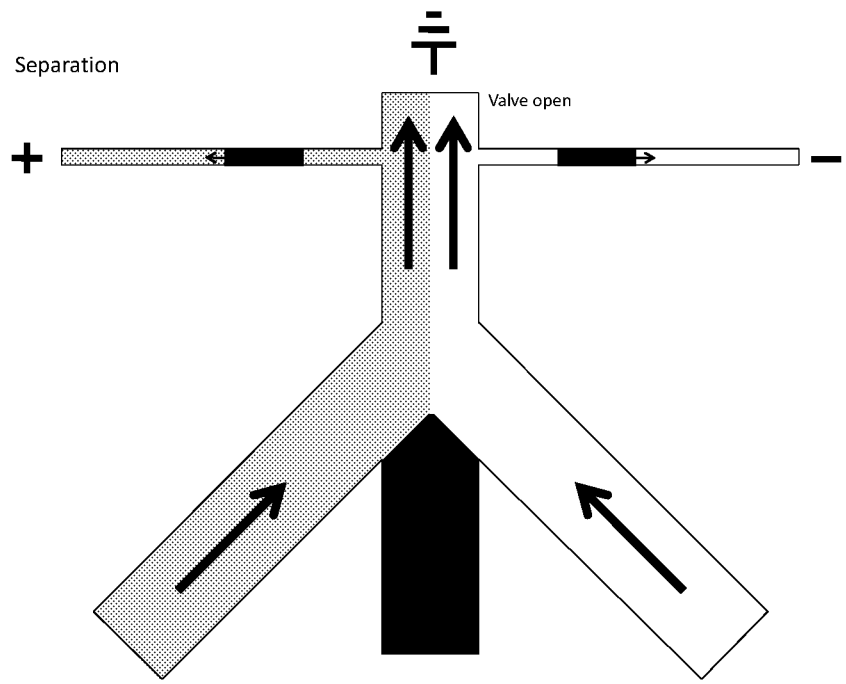

With this feature in place, the following sequence of steps can be used for performing the electrophoretic separation for the embodiment where the analytes are cations and anions:

priming the two separation channels with background electrolyte, by concurrently introducing background electrolytes from the first and second background electrolyte injection ports into their respective portions of interface zone of the fluid channel initially with the fluid channel outlet opened, and then with the fluid channel outlet closed to hydrodynamically force background electrolyte from the first background electrolyte port into the first separation channel and background electrolyte from the second background electrolyte port into the second separation channel (see FIG. 8A);

loading the sample (represented by solid black shading) into the interface zone of the fluid channel by injecting the sample through the single sample injection port to pass into the interface zone of the fluid channel with the fluid channel outlet open (see FIG. 8B);

loading the sample into the two separation channels (FIG. 8C);

concurrently introducing background electrolyte from the first and second background electrolyte injection ports through the fluid channel with the fluid channel outlet open and into their respective portions of the interface zone of the fluid channel (without the concurrent flow of sample through the sample injection port) (see FIG. 8D);

applying a voltage potential across the two separation channels to simultaneously effect a separation of the anions present in the sample in the first separation channel, and effect a separation of cations present in the sample in the second separation channel (see FIG. 8E); and detecting the presence of the separated anions through the first detector, and the presence of the separated cations through the second detector.

Usually, background electrolytes of two different compositions will be used as the first and second background electrolytes. This results in each separation taking place simultaneously in the presence of different background electrolytes. However, it is possible to use background electrolytes of the same composition in the system.

The step of loading the sample into the two separation channels may take place hydrodynamically or electrophoretically. If hydrodynamic, the fluid channel outlet is closed and the sample is injected through the sample injection port, without the concurrent flow of background electrolyte, and into the separation channels. If electrophoretic, a voltage is applied to electrophoretically inject the sample into the separation channels. Hydrodynamic sample loading (i.e. injection) into the separation channels is represented schematically in FIG. 8C.

Figure 9A:
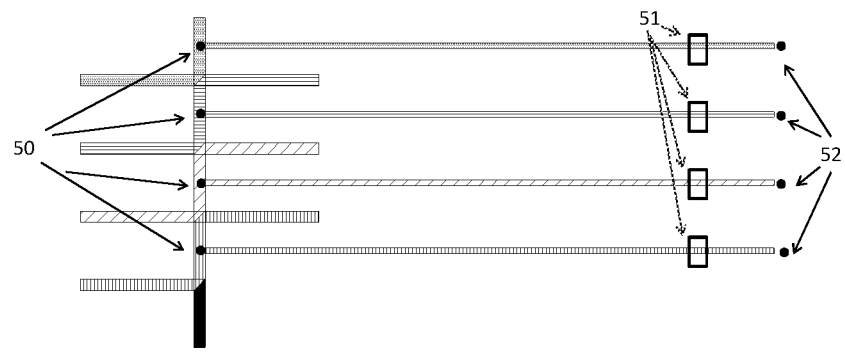
FIG. 9 is a set of schematic diagrams illustrating a microchip electrophoresis system for delivering 4 background electrolytes to each of 4 separation channels simultaneously, in accordance with a further embodiment of the invention.
Figure 9B:
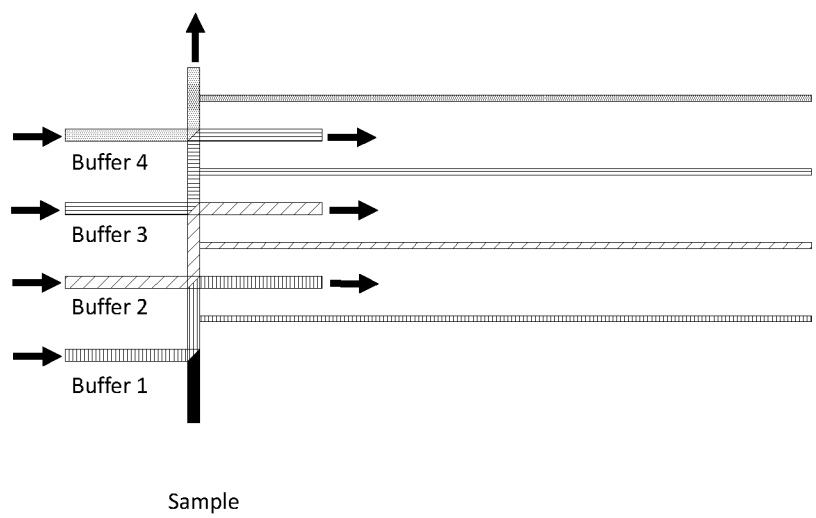

The microchip design for a four-way separation of one embodiment is illustrated in FIG. 9. In this design, the microchip contains:

a main fluid channel which extends across the width of the chip to one end (extending upwardly at the left end of FIG. 9A), a sample injection port at one end of the main fluid channel (sample is injected at the lower end of the main fluid channel shown in FIG. 9A);

four background electrolyte inlet channels extending towards the main fluid channel (extending laterally on the left hand side of the main fluid channel in FIG. 9A), which are in fluid communication with a sample injection port, four background electrolyte channel outlets (three channels extending laterally away from the main fluid channel on the right hand side, and the fourth being defined by the main channel fluid outlet extending upwardly, in FIG. 9A), four separation channels that extend laterally outwardly (in a perpendicular direction) from the main fluid channel, positioned in advance of the background electrolyte channel outlets (represented by the thin lines extending away from the right hand side of the main fluid channel), four detectors 51;

ground electrodes 50 (each represented by a dot at the entrance to each separation channel); and four high voltage electrodes 52.

Different shading is used for the fluid pathway for each of the background electrolytes in FIG. 9, showing a "zig-zag" pathway for each background electrolyte.

Fluid outlets are also provided at the outlet ends of the separation channels, for draining liquids away from the separation channels on the microchip.

The arrangement of the background electrolyte channels is such that when respective background electrolytes are injected via the injection ports and into the main fluid channel, the background electrolytes will flow concurrently in their own streams, and without mixing, through the fluid channel. The interface zone in this embodiment encompasses the regions of the inlets to the four separation channels, and a different electrolyte flows past each of the separation channel inlets, in separate streams, one after the other through segments of the main fluid channel. This is shown by the shaded flow of streams of background electrolyte in FIG. 9B. Since the separation channel entrances are located in a portion of the interface zone (in segments of that zone, as shown in FIG. 7) through which only one of the background electrolyte compositions pass, just the background electrolyte that passes through that portion of the interface zone will flow (when subjected to the required hydrodynamic force) into the subject separation channel.

Figure 9C:
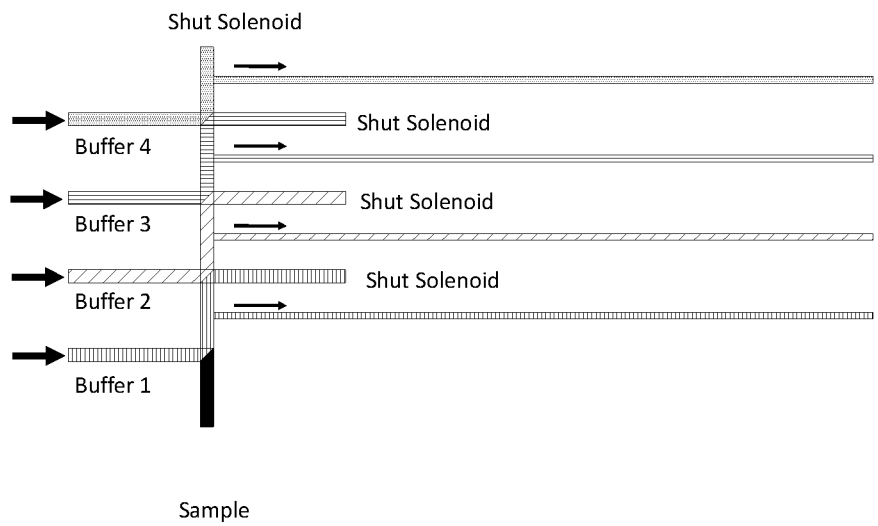
Figure 9D:
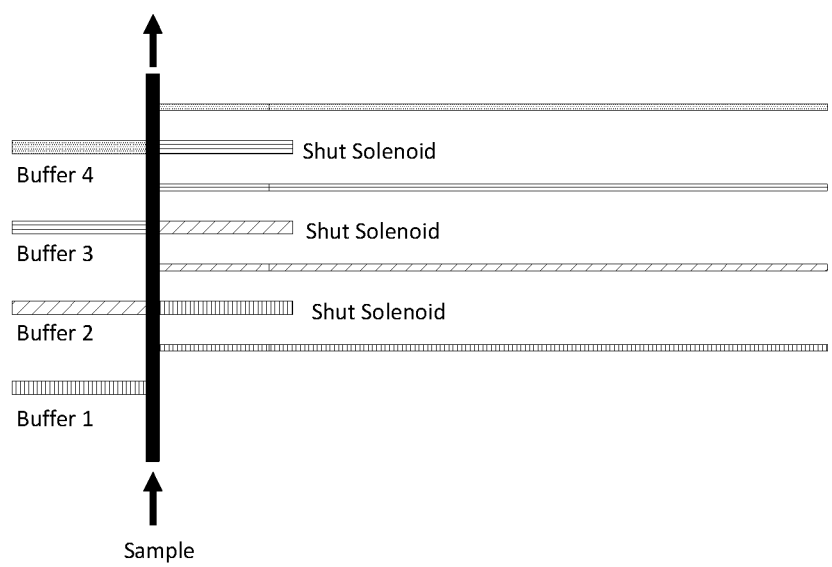
Figure 9E:
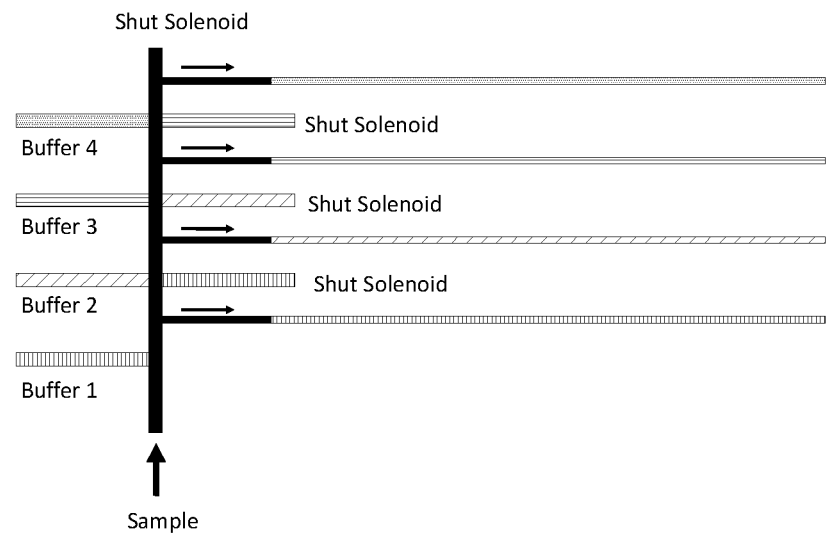
Figure 9F:
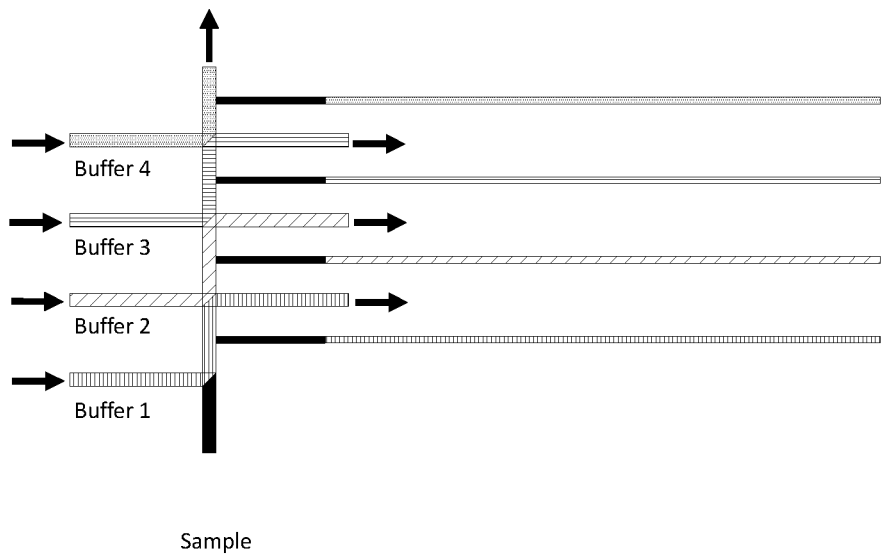
Figure 9G:
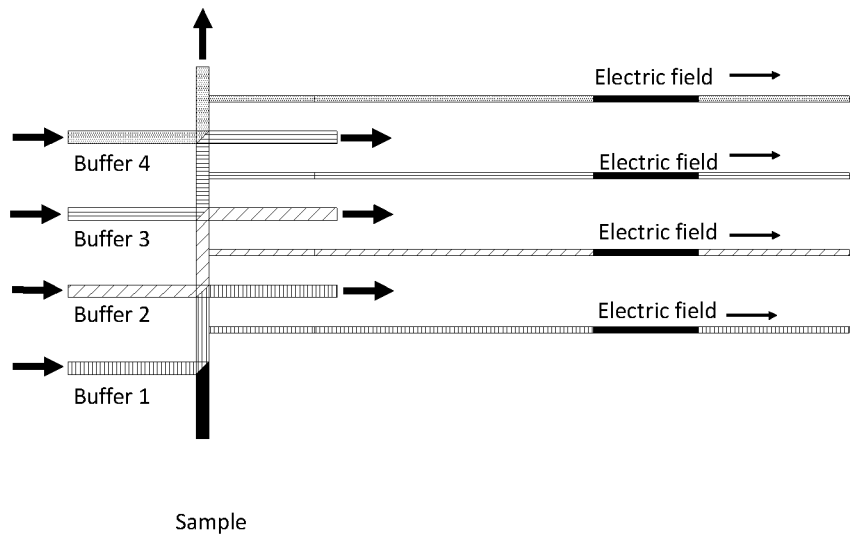

After loading the background electrolytes into the separation channels, the sample is injected through the sample inlet and through the main channel, as shown in FIG. 9C. Then, as shown in FIG. 9D, the sample is injected into the separation channels. In the embodiment of FIG. 9D, this is conducted electrophoretically through the application of a voltage across the separation channel, although hydrodynamic injection can alternatively be used. In a following step, shown in FIG. 9E, the four streams of background electrolyte are introduced from the first, second, third and fourth background electrolyte injection ports, through the main fluid channel (with the respective background electrolyte outlets and the main fluid channel outlet open), and into their respective portions of the interface zone of the fluid channel. This takes place without the concurrent flow of sample through the sample injection port. This results in a plug of sample passing into each of the separation channels. Then, as shown in FIG. 9F, a voltage is applied to effect the electrophoretic separation of analytes in the plug of sample in each separation channel (or "column"). The analytes are detected by the detector as they pass through the detection zone of the separation channels.

The microchip used in the above embodiments may be constructed by any suitable technique including, without limitation, micromachining, lithography, casting, embossing or similar, or through a combination of such techniques. The channels are generally created in one face of the microchip, and a lid is bonded thereto.

The fluid channel diameter is typically similar to those used in the microchip system compared to that utilised in capillary electrophoresis, described above. However, the channels in this case may be generally rectangular or semi-circular in cross-section (rather than circular), and have a depth that is smaller than the width. Where the microchip is based on a plastic substrate, channels of rectangular cross-section may be preferred, and when the substrate is glass, semi-circular channels may be preferred. The separation channel widths (being the longer dimension for the rectangular channels or the diameter/2 times radius dimension of the semi-circular channels) are typically also about the same as the diameter dimensions noted above for channels of a circular cross-section. Typical diameters for such microchip the main fluid channels are around 300 to 500 µm (and may range from 50 to 500 µm). The depth (corresponding to the radius dimension or maximum depth in the case of semi-circular channels) is typically around 50 µm (thus, between about 10 and 100 µm, or between 30 and 70 µm). Typical diameters for the separation channels are 50 µm (and thus these may range from 10 to 100 µm). The depth of the separation channels may be the same as that for the main fluid channel, or smaller in the case of semi-circular channels. It is noted that the separation channel has a diameter that is typically less than 30% of the diameter of the main fluid channel, for example less than 25%, or less than 20%, compared to the main fluid channel diameter, as this helps to prevent fluids passing through the main fluid channel to pass into the separation channels without hydrodynamic or electrokinetic assistance.

The electrodes may be of any suitable type and design. The electrodes may be contactless electrodes.

Control System

In the case of all embodiments described above, a control system, such as a computer, is used to operate the apparatus or device. The control system may therefore control the stages of operation of the device, including control of the injection system (such as the valve position), control of the pump operation (and speed of flow of background electrolyte or electrolytes), control of the outlet valve for the fluid channel (if present), application of the voltage potential and so forth. The control system may also control the detection system, including processing of the signal received by the detector, and converting that signal into a visual representation (on a display or otherwise). The control system may comprise a personal computer or a dedicated control system.

In the electrophoresis system for the simultaneous separation and detection of anions and cations in a sample, the controller suitably controls the injection system, flow of background electrolyte and the voltage applied to produce the following sequence of steps:

introducing background electrolyte into the interface zone of the fluid channel and hydrodynamically forcing the background electrolyte into first and second separation channels to prime the two separation channels with background electrolyte;

injecting the sample through the single sample injection port to pass into the interface zone of the fluid channel to load the sample into the interface zone of the fluid channel;

loading the sample into the two separation channels;

introducing background electrolyte through the fluid channel and into the interface zone of the fluid channel;

applying a voltage potential across the two separation channels to simultaneously effect a separation of the anions present in the sample in the first separation channel, and effect a separation of cations present in the sample in the second separation channel; and detecting the presence of the separated anions through the first detector, and the presence of the separated cations through the second detector.

The above sequence of steps can be modified as required for the separation of analytes other than cations and anions.

In one embodiment, the system comprises two or more background electrolyte reservoirs for storing two background electrolytes, and the controller controls the introduction of the two background electrolytes into and through the fluid channel.

In the system that involves the delivery of two or more different background electrolytes, the controller suitably controls the injection system, flow of background electrolyte and the voltage applied to produce the following sequence of steps:

concurrently introducing background electrolytes from the first and second background electrolyte injection ports into their respective portions of interface zone of the fluid channel, to hydrodynamically force background electrolyte from the first background electrolyte port into the first separation channel and background electrolyte from the second background electrolyte port into the second separation channel;

injecting the sample through the single sample injection port to pass into the interface zone of the fluid channel to load the sample into the interface zone of the fluid channel;

loading the sample into the two separation channels;

concurrently introducing background electrolyte from the first and second background electrolyte injection ports through the fluid channel and into their respective portions of the interface zone of the fluid channel;

applying a voltage potential across the two separation channels to simultaneously effect a separation of the anions present in the sample in the first separation channel, and effect a separation of cations present in the sample in the second separation channel; and detecting the presence of the separated anions through the first detector, and the presence of the separated cations through the second detector.

Again, for the separation of analytes other than anions and cations, the references to cations and anions can be replaced with references to analytes.

In each case, the controller may present to the user on an associated display a plurality of different desired profiles for which to select. Upon receipt of a selection via an input device such as a mouse, keypad or the like, the controller uses the selected desired profile to retrieve the relevant operation parameters from a look up table stored in a memory of the controller. That is, in one example, the controller is in data communication with a user interface having a display and one or more input devices. The controller has a processor that processes computer readable instructions stored in an associated, tangible memory to present requests for input to a user, receive one or more inputs via the input device(s) and control the radiation source in accordance with the input and the instructions stored in the memory. The term "processor" is used to refer generically to any device that can process inputs in accordance with stored instructions to control a radiation source and can include: a microprocessor, microcontroller, programmable logic device or other computational device, a general purpose computer (e.g. a PC) or a server.

The system may be in the form of a device or apparatus. The device may be a one-part device, or in separate parts.

The control system preferably enables at least 10 sample runs per hour, preferably at least 12, or at least 14. 17 sample runs per hour have been achieved to date in the system described in the Examples below.

EXAMPLES

The present invention will now be described in further detail with reference to the following examples which demonstrate the principles underlying the invention, and specific embodiments of the invention. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Example 1

1. Experimental
1.1 Apparatus

A SI-CE system (sequential injection capillary electrophoresis system) was developed in-house. A schematic drawing of the bench top system is depicted at FIG. 1 (a). A double syringe pump (Harvard Apparatus, Model 33, Holliston, Mass., USA) was used to deliver sample and background electrolyte (BGE) to the system. Two 20 mL plastic syringes (Livingstone, Holliston, Mass., USA) or glass syringes (Hamilton, Reno, Nev., USA) were used. A two position injector valve (MXP-7980, Rheodyne, Oak Harbor, Wash., USA) enabled the alternate delivery of sample or BGE to the separation interface. A commercial PEEK cross piece connection (P-729, Upchurch Scientific, Oak Harbor, Wash., USA) was used to interface the two capillaries to the flow system. A 20 mm stainless steel tube cut from a syringe needle (0.51 mm i.d.) served as an outlet and ground electrode. An isolation valve (HP225K021, NResearch, West Caldwell, N.J., USA) on the crosspiece outlet line allowed for the online flushing of capillaries for equilibration and cleaning.

Two separate fused silica capillaries of 50 µm i.d. (Polymicro, Phoenix, Ark., USA) were utilised for the anions and cation separations. The distance between the two capillary tips within the interface was fixed by utilising a piece of capillary (360 µm o.d.) inserted through the flow-through arm of the crosspiece. The outlet sides of both capillaries were inserted into a 20 mL glass vial containing 15 mL of BGE.

For online sampling, the outlet line from a quaternary gradient HPLC pump (Alltech 727, Grace Division Discovery Science, Archerfield, QLD, AUS) was plumbed to the two position valve in lieu of the sample syringe. The quaternary pump sampled directly from an overflow container on one inlet line and an internal standard container on a second inlet line. BGE was delivered to the system via a milliGAT pump/MForce controller (MG-5, GlobalFIA, Fox Island, Wash., USA) to overcome the volume limitations of the syringe pump. The online sampling setup is shown at FIG. 1 (b).

Two commercial $C^4D$ detectors (Tracedec, Innovative Sensor Technologies, Strassahof, Austria) were used, one detector per capillary. Detection parameters were set for the entire system study at: Frequency high; voltage −6 dB; gain 100%, offset 000; filter: frequency ⅓ and cut-off 0.02.

An Agilent 35900E A/D convertor (Agilent Technologies, Waldbronn, Germany) was used to interface the $C^4D$ signals with the Agilent Chemstation software used to record and analyse the signal. Separation on each capillary was driven by either a Spellman CZE2000 or CZE1000 high voltage power supply (Hauppage, N.Y., USA) working under normal polarity (+) for the cation separation or reversed polarity (−) for the anion separation respectively. Electrodes were immersed in their respective outlet vials.

The system was controlled via a personal computer using an RS232 serial connection for the syringe pump (RS422 serial connection for milliGAT pump). The injection valve, isolation valve and high voltage power supplies were interfaced to the computer via a NI USB-6212 data acquisition device (National Instruments, Austin, Tx, USA). Total system control, less data acquisition, was achieved using in-house written software (Labview 8.1, National Instruments).

The system was not thermally controlled and all experiments were performed at ambient room temperature.

2.1. System Operation

Sample injection was made sequentially and typical separation sequence steps are detailed in Table 1. Starting from a primed condition with the interface and capillaries completely filled with BGE, the interface was filled with sample followed by application of a high voltage for 1 s to inject sample anions and cations onto their respective separation capillaries. After injection, the sample was flushed from the interface at 500 µLmin$^{-1}$ and reduced to 50 µLmin$^{-1}$ when the separation voltage was applied. The time and flow rates were selected to minimise injection time and the consumption of reagents. Migration times of analytes were not affected by the flow rate of BGE during separation between the range of 50 and 500 µLmin$^{-1}$ when utilising 55/50 cm×50 µm i.d. capillaries under the final separation conditions.

TABLE 1

| Step | Operation | valve position | Volume dispensed (µL) | Time (s) | Flow rate (µLmin$^{-1}$) | Solenoid valve |
|---|---|---|---|---|---|---|
| 1 | Sample introduction | 2 | 83 | 5 | 1000 | Open |
| 2 | Injection | 2 | N/A | 1 | 1000 | Open |
| 3 | Flushing of interface | 1 | 83 | 5 | 1000 | Open |
| 4 | Electrophoretic Separation | 1 | 150 | 180 | 50 | Open |
| 5 | Capillary and interface flush | 1 | 42 | 5 | 500 | Closed |
| 6 | Pressure equilbration | 1 | 0 | 5 | 0 | Open |

A hydrodynamic flush sequence was incorporated to physically clean and re-equilibrate the capillary surface between runs. This was achieved by closing the isolation valve and flowing BGE at 500-1000 µLmin$^{-1}$ for 5 s to build sufficient pressure in the cross piece interface to flush the capillaries. Following the high flow flush of the capillaries, the isolation valve was reopened and a 5 s pause period was observed to allow the system to equilibrate to ambient pressure prior to the next sample injection. This flush step provided three benefits. Firstly it enabled the ability to set the analysis time by allowing unwanted analytes to be flushed past the detector to ensure that they did not interfere with subsequent runs. Secondly, it provided a physical clean of the capillaries to remove partial blockages and air bibbles and finally, it re-equilibrated the capillary surface between runs which significantly increased baseline stability from run to run.

2.2 Chemicals

All reagents were analytical reagent grade obtained from Sigma-Aldrich (Sydney, AUS) and were used as supplied unless stated otherwise. Solutions were prepared in Milli-Q water (Millipore, Bedford, Mass., USA). Given that separations of both anions and cations were conducted simultaneously, standard solutions were prepared from available salts to achieve an approximately equal concentration of all 12 analytes of interest. Anion standard solutions of 1000 mgL$^{-1}$ were prepared by the dissolution of NaClO$_4$, KClO$_3$, Mg(NO$_3$), NaF, KH$_2$PO$_4$(BDH, VIC, AUS), CaCl$_2$.2H$_2$O (AJAX, NSW, AUS), (NH$_4$)$_2$SO$_4$ (H&W, Essex, GBR).

Analytes were selected to allow a broad and general study of common inorganic ions of interest to water monitoring, explosive analysis and common environmental background ions. To this end, a standard analyte mix of PO$_4^{3-}$, F$^-$, SO$_4^{2-}$, ClO$_3^-$, ClO$_4^-$, Ca$^{2+}$, K$^+$ (all 5 ppm), Cl$^-$ (9 ppm), Na$^+$ (7 ppm), NH$_4^+$ (2 ppm) and Mg$^{2+}$ (1 ppm) was prepared. Sodium-1-methylsulfonate monohydrate (MSA) and Li$_2$CO$_3$ were used as internal standards. Apart from filtration, no sample pre-treatment occurred prior to injection. The three studied BGEs were 70 mM (tris(hydroxymethyl) aminomethane (Tris))/70 mM N-Cyclohexyl-2-aminoethanesulfonic acid (CHES), pH 8.6, 50 mM 2-(N-morpholino) ethanesulfonic acid (MES)/50 mM L-histidine (His), pH 6.1, and a 50 mM acetic acid (AA)/10 mM His, pH 4.2. Hexadimethrine bromide (HDMB) was employed to coat the walls of the fused-silica capillaries in order to reverse the electroosmotic flow when required.

2.3. Electrophoretic Procedures

Prior to first use, all fused silica capillaries were conditioned off-line by flushing at 0.5 µLmin$^{-1}$ with 1 M NaOH for 5 min and Milli-Q water for 5 min. Where HDMB coatings were employed, these capillaries where then coated with a 5% aqueous solution of HDMB for 5 min, followed by water for 5 min. After both capillaries were conditioned/coated, they were assembled at the cross-piece and equilibrated with BGE in order to avoid cross contamination of any cationic surfactant onto the bare fused silica capillary used for the cation separation.

Linear Poly Acrylamide (LPA) coated capillary of 50 µm i.d. was purchased from Polymicro Technologies. They were conditioned by flushing at 0.5 µLmin$^{-1}$ with Milli-Q water for 10 minutes. In all cases, capillary equilibration was achieved by flushing capillaries with BGE for 30 minutes at 5 µLmin$^{-1}$ after assembly of the separation interface.

3. Results and Discussion

Figure 2:
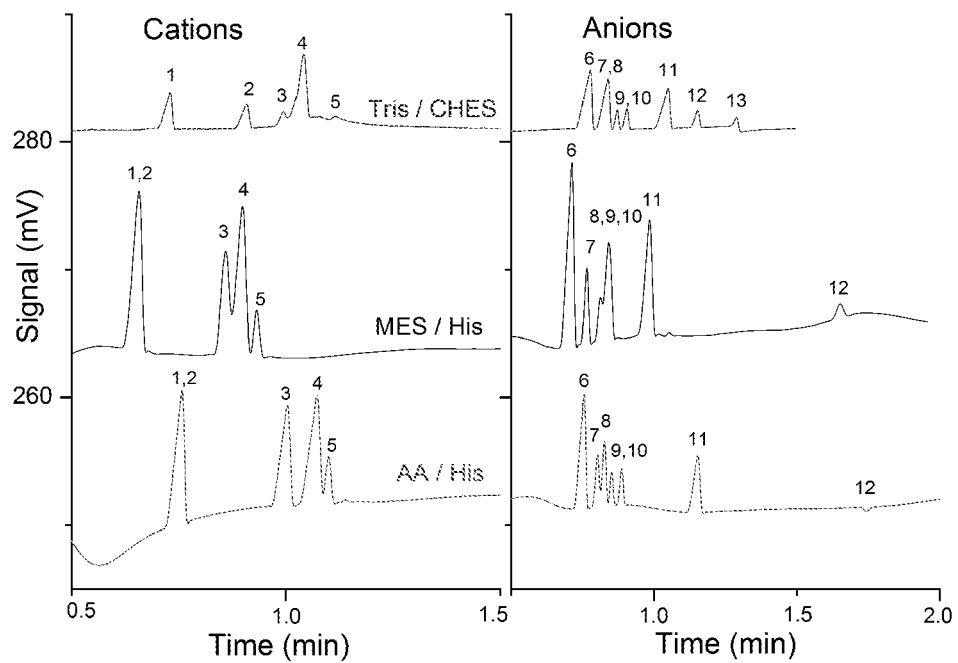
FIG. 2 shows electropherograms for simultaneous suppressed-EOF separations conducted on LPA coated capillaries for cations (left) and anions (right). CE conditions (both): capillary 50 μm id, total length of 40 cm (25 cm to detector), +/−30 kV cation/anion separation respectively. Background electrolytes: Tris/CHES=70 mM Tris/70 mM CHES at pH 8.6, MES/His=50 mM MES/50 mM His at pH 6.1, AA/His=50 mM Acetic acid/10 mM his at pH 4.2. (1) $K^+$, (2) $NH_4^+$, (3) $Ca^{2+}$, (4) $Na^+$, (5) $Ca^{2+}$, (6) $Cl^-$, (7) $NO_3^-$, (8) $SO_4^{2-}$, (9) $ClO_4^-$, (10) $ClO_3^-$, (11) $F^-$, (12) $PO_4^{2-}$, and (13) $CO_3^{2-}$.

The apparatus and system outlined above was developed to allow the simultaneous injection and separation of anions and cations. A commercial cross piece was used to interface the separation capillaries, and capillaries with an ID of 50 µm were used as these had sufficient backpressure to restrict any hydrodynamic flow through the capillary. Functionality of the device was also increased by inclusion of an isolation valve which could be shut to allow both capillaries to be rapidly flushed. Demonstration of the functionality of this approach is shown in FIG. 2. This shows the simultaneous separation of 5 cations (K$^+$, NH$_4^+$, Ca$^{2+}$, Na$^+$, Mg$^{2+}$) and 8 anions (Cl$^-$, NO$_3^-$, SO$_4^{2-}$, ClO$_4^-$, ClO$_3^-$, F$^-$, PO$_4^{2-}$, CO$_3^{2-}$) in three previously studied BGEs utilising C$^4$D detection.

The first BGE selected for use in the separation of cations and anions in these experiments comprised 10 mM L-histidine (His) and 50 mM acetic acid at pH≈4 with various concentrations of 18-Crown-6 ether. A second buffer selected for use comprised of 20 mM MES/20 mM His buffer at pH 6.1. This buffer is popular for the separation of cations and has been used in microchip CE separations of both anions and cations. Here, the concentration was adjusted to 50 mM MES/50 mM His in order to increase signal response in this system. The third and final BGE selected for use consisted of 70 mM Tris and 70 mM CHES at pH 8.6, which is an effective BGE for the separation of inorganic anions and low molecular weight organic acids. As can be seen from the figure, there is excellent separation of both the anions and the cations and the simplicity of this approach for simultaneous separation of anions and cations from the one sample injection point can be clearly seen. One of the limitations that this approach has is that the same BGE chemistry must be used for both anions and cations, and thus selection of the most appropriate BGE will be application specific. The best BGE for the separation of the selection of ions here will be discussed further below after consideration of the influence of EOF. In any event, this limitation is overcome when the two electroloyte system described herein is used.

3.1. Capillary Wall Coatings

The main difference between the approach described here and DOI-CE is that two separation capillaries are used instead of one. This enables the use of various wall coatings and hence, separate EOF conditions for anion and cation separations which offers a degree of flexibility with which to optimise both separations.

To evaluate the influence of different surface chemistry and hence different EOF, separations of the standard analyte mix were carried out in the three BGEs mentioned above with three different separation capillaries: normal EOF in unmodified fused silica, low EOF in LPA coated capillary, and reversed EOF in HDMB coated capillaries. Cation separations were only examined in fused silica and LPA coated capillaries because a counter-EOF study of cation separations had the effect of drawing HDMB molecules into the separation interface (as EOF was greater than the mobility of HDMB) causing contamination of the interface and the opposite separation capillary.

Figure 3:
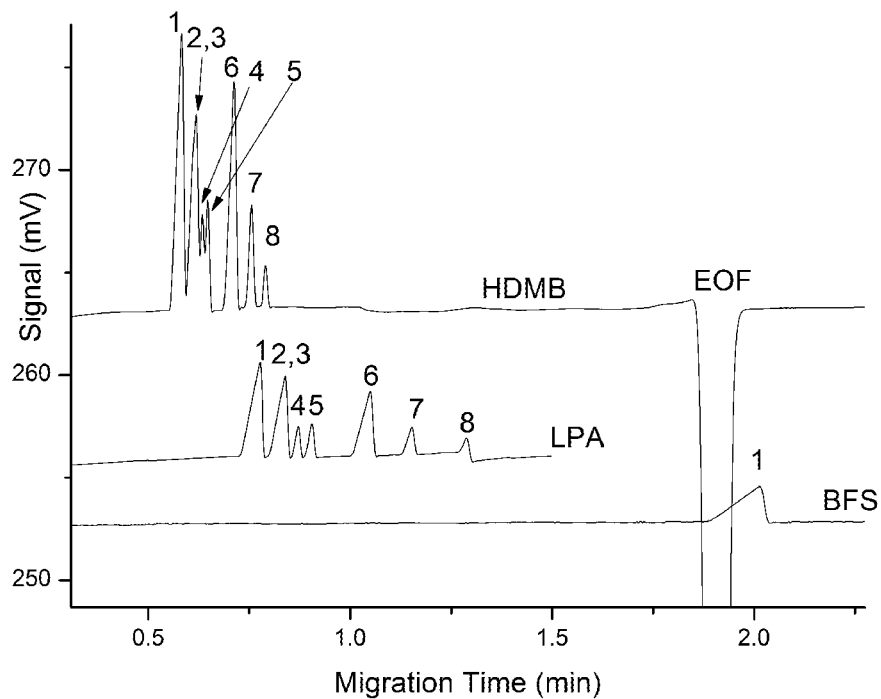
FIG. 3 shows electrograms for anion separations in Tris/Ches buffer in HDMB coated, LPA coated and BFS capillaries. All other separation conditions and analyte identities are as for FIG. 2.

The ability to use a capillary with a different surface charge will have the most pronounced effect on the separation of the anions at high pH and this can be seen from FIG. 3. The migration time of $Cl^-$ changes from 120 s in the unmodified fused silica capillary, to 45 s in LPA and 35 s in the HDMB coated capillary. The slowest peak, phosphate, changed from 530 s, 120 s and 46 s respectively, in the same capillaries. The use of HDMB coated capillaries for the separation of anions and unmodified fused silica for cations presents the unique ability to simultaneously separate both anions and cations from the same injection point in a co-EOF manner, which is not possible by any other approach in CE or ME.

Figure 4:
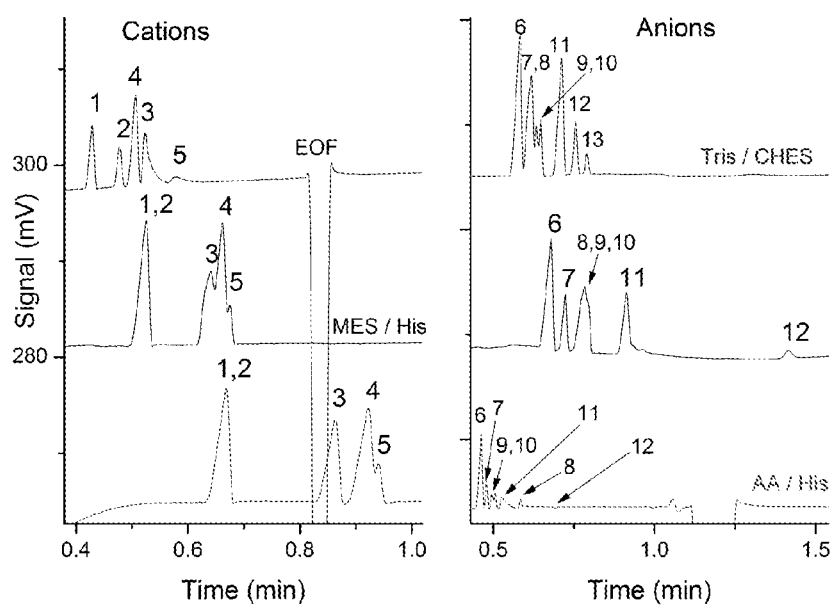
FIG. 4 shows electropherograms for simultaneous co-EOF separations conducted on bare fused silica capillaries for cations and HDMB coated capillaries for anions. All other separation conditions and analyte identities are as for FIG. 2.

FIG. 4 shows the results of the simultaneous co-EOF separation of the standard anions and cations in the three different BGEs. As would be expected, the migration times of all cations increased with buffer pH due to an increase in the magnitude of the EOF. It would be expected that only minor influences on the migration times of the anions would be observed, however, this was not always the case. When performing co-EOF separations in both capillaries, of particular interest was the variation in migration times (especially anions) between replacements of capillaries. This variation was most noticeable in the Tris/CHES BGE where cation separation EOF was the greatest (and the anion capillary EOF was considerable). It was found that variations in migration times of cations between rebuilds were relatively small (<15%) in comparison to the variations in migration times of anions (up to 30%). Whilst hydrodynamic, electrodynamic and EOF forces exist at the injection interface during injection and separation, these results indicated that the dominant force affecting migration times was due to the competition between EOF in both directions. In the case of the co-EOF Tris/CHES system, the EOF generated by the bare fused silica was significantly greater than the pH independent EOF generated by the HDMB coated capillary. Where suppressed EOF conditions in both capillaries, or where co-EOF conditions in the cation capillary and suppressed EOF conditions in the anion capillary are concerned, rebuilds of the interface demonstrated no significant change in the migration times of either anions or cations. These results indicate that precise capillary alignment (including positioning of the entrances an equal distance from the ground electrode) in the interface zone is critical under conditions of high EOF in both directions.

Once built, migration times were repeatable over the lifetime of the capillary wall coating with inconsistencies only when capillaries needed to be replaced. Improvements in how to physically define the positions of the capillaries may alleviate this issue, but was not studied further in this work.

3.2. Optimum Conditions for Simultaneous Separation

With regards to selectivity and peak shapes, excellent selectivity was observed for the cations in Tris/CHES, and $K^+$ and $NH_4^+$ could be separated without using an additive which is explained by the partial deionization of the $NH_4^+$ ions which occurs at pH values above 8[14]. Their separation can be easily facilitated in the AA/His and MES/HIS BGEs with the addition of 18-crown-6 ether (through complexation with potassium) with nil observed effect on the anion separation, however this was not included here to simplify comparison of the systems. The drawback of the Tris/CHES system for cations was the significant tailing for both $Ca^{2+}$ and $Mg^{2+}$ most likely due to the formation of their hydroxides. The separation selectivity of the cations was slightly better in AA/His and would be the BGE of choice if only the separation of cations was required.

With regards to separation of the anions, the Tris/CHES buffer provided fast migration times, good signal response and the most stable baseline of all three buffers, however satisfactory resolution of $NO_3^-$ and $SO_4^{2-}$ was not achieved over a maximum run time of three minutes. Further, the HDMB coating would last no more than 80 runs before a 10% increase for the slowest analyte's migration time ($HPO_4^{2-}$) relative to the first run occurred. Eventually, the EOF signal in the anion separation would disappear completely accompanied by a significant increase in migration times for the anions, indicating a significant degradation of the surface coating. This required a complete replacement of the capillary, as to avoid contamination of the interface and the cation separation capillary with HDMB, the BGE could not contain any surface modifying additive and the interface could not be flushed between each separation. All HDMB coated capillaries had to be performed off-line and inserted into the interface after flushing the HDMB from the capillary to avoid contamination. This trend was most prominent at high pH but was observed for all BGEs, and is not surprising as HDMB coatings are dynamic. Practically, this limited the appeal of a HDMB coating for long term use.

In the MES/His buffer, anion selectivity was unsatisfactory over a maximum separation time of three minutes. The acetic acid/Histidine buffer provided for suitable resolution of all anionic species although the migration time of $HPO_4^{2-}$ was significantly greater than that of the next slowest analyte ($SO_4^{2-}$) and significant tailing of the $F^-$ ion occurred for HDMB coated capillaries, suggesting a wall interaction with the positively charged HDMB coating. The selectivity of $SO_4^{2-}$ was also altered from the same separation carried out in either BFS or LPA coated capillaries (compare to FIG. 4) presumably due to interaction with the HDMB.

Whilst co-EOF conditions in both directions promised faster separations, the short capillary wall coating life time in the anion channel eliminated the HDMB option for extended operation applications. Given that the total separation time was ultimately governed by the migration time of the slowest species ($HPO_4^-$) it was decided that the slower migration time afforded for the cationic separation in LPA would help better resolve $Na^+$ and $Mg^{2+}$ peaks.

For the reasons outlined above, a suppressed EOF system (LPA coated capillaries) utilising an AA/His/18-crown-6 ether BGE was chosen to evaluate the analytical performance of the system

4. Performance

4.1 Sequential Injection Analysis of Environmental Samples

Using the conditions above as a starting point, in order to fully resolve all of the ions in the LPA coated capillaries using a BGE with 50 mM AA, 10 mM His and 2.5 mM 18-crown-6 ether, the capillary lengths were extended to 55 cm (35 cm effective length) for the cation separation and 50 cm (28 cm effective length) for the anion separation. To improve the analytical performance for real samples, two internal standards (IS) were used to allow correction for the well known sample matrix bias that occurs with electrokinetic injection. The IS chosen for the cation separation was $Li^+$ (5 ppm), as $Li_2CO_3$, with the benefit that the $CO_3^{2-}$ ion would be protonated at pH 4.2 and not be seen in the anion separation. Methyl Sulfonic Acid ($C_3H_8SO_3^-$) (10 ppm) was chosen as the anionic IS. A representative electropherogram for the standard separation is given at FIG. 5($a$).

Figure 5:
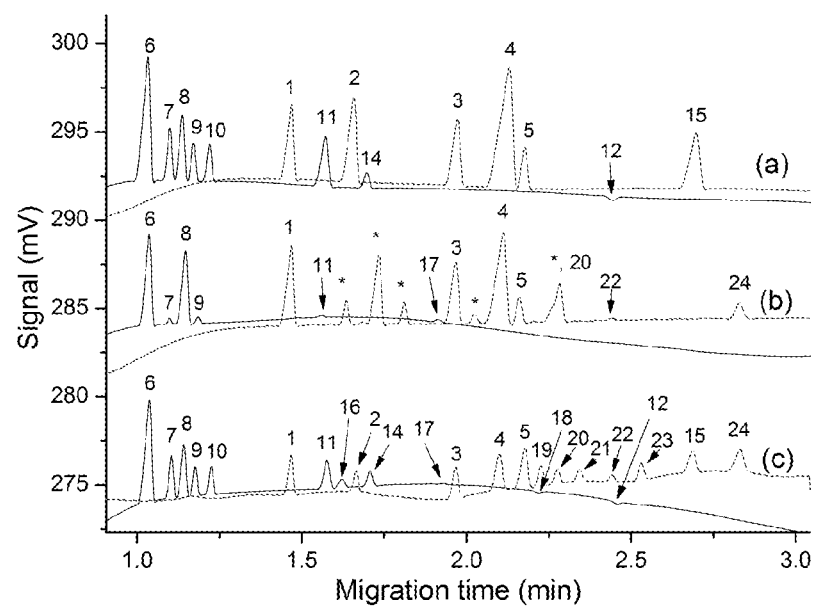
FIG. 5 shows electropherograms for separations of (a) standard analyte mix with Internal Standards, (b) process water from Zinc manufacturing plant and (c) 23 small ions. In all electropherograms, anion signals are overlayed with corresponding cation signals. Note the ion identities to establish the anion and cation signals in the electrographs. CE conditions for a, b and c: Cation capillary 50 μm i.d LPA coated, I/L=35/55 cm, Anion capillary 50 μm i.d LPA coated, I/L=28/50 cm, U=−/+30 kV (Cation/Anion respectively). Background electrolyte: 50 mM Acetic acid/10 mM His at pH 4.2. Analyte identities: (1) $NH_4^+$, (2) $K^+$, (3) $Ca^{2+}$, (4) $Na^+$, (5) $Mg^{2+}$, (6) $Cl^-$, (7) $NO_3^-$, (8) $SO_4^{2-}$, (9) $ClO_4^-$, (10) $ClO_3^-$, (11) $F^-$, (12) $PO_4^{2-}$, (13) $CO_3^{2-}$, (14) $CH_3SO_3^-$ [IS], (15) $Li^+$[IS], (16) $(CrO_4)^{2-}$, (17) $MoO_4^{2-}$, (18) $C_3H_8SO_3^-$, (19) $Mn^{2+}$, (20) $Zn^{2+}$, (21) $Sr^{2+}$, (22) $Cd^{2+}$, (23) $Cr^{3+}$, and (24) $Be^{2+}$. *: unidentified ion.

These same separation conditions provided for very good separations of various environmental samples including river and lake samples (not shown), tap water (shown in FIG. 6) and Zinc processing plant water samples taken from various stages of production, one of which is shown in FIG. 5($b$). Within a total separation time of 3 min, FIG. 5($c$) demonstrates the simultaneous separation of 23 anions and cations, indicating the potential of the system for a range of applications beyond those discussed here.

Migration time and peak area reproducibility data is given in Table 2 and is based upon analysis of every 10$^{th}$ run out of 101 consecutive separations of the standard analyte solution (n=10) performed continuously over a 6 hour period. LODs were calculated from injection of a 10 times diluted sample of the standard analyte solution (≈0.5 ppm for most analytes) and are calculated at a signal:noise ratio of 3. LODs for most analytes are between 0.01 and 0.05 mgL$^{-1}$. These values were significantly better than the 0.1-1.7 mgL$^{-1}$ values obtained by indirect absorbance detection and slightly better than the 0.04-0.08 mgL$^{-1}$ values obtained using a CE system using C$^4$D detection.

TABLE 2

| | Migration time (n = 10) | peak area (n = 10) | Range | Calibration $R^2$ | LOD (S/N = 3, |
|---|---|---|---|---|---|
| | (min) | RSD (%) | RSD (%) | (ppm) | | mg/L) |
| $NH_4^+$ | 1.44 | 0.59 | 4.87 | 0.1-5 | 0.998 | 0.016 |
| $K^+$ | 1.62 | 0.51 | 6.35 | 0.1-5 | 0.998 | 0.040 |
| $Ca^{2+}$ | 1.93 | 0.51 | 4.06 | 0.1-5 | 0.991 | 0.030 |
| $Na^+$ | 2.09 | 0.33 | 1.48 | 0.1-5 | 0.999 | 0.035 |
| $Mg^{2+}$ | 2.13 | 0.47 | 3.53 | 0.1-5 | 0.991 | 0.013 |
| $Li^{2+}$ | 2.65 | 0.46 | 3.71 | 0.1-5 | 0.994 | 0.032 |
| $Cl^-$ | 1.02 | 0.23 | 3.83 | 0.1-5 | 0.996 | 0.022 |
| $NO_3^-$ | 1.09 | 0.23 | 7.17 | 0.1-1 | 0.995 | 0.006 |
| $SO_4^{2-}$ | 1.12 | 0.26 | 6.81 | 0.1-1 | 0.992 | 0.005 |
| $ClO_4^-$ | 1.16 | 0.26 | 2.84 | 0.1-1 | 0.995 | 0.010 |
| $ClO_3^-$ | 1.20 | 0.27 | 4.41 | 0.1-1 | 0.995 | 0.009 |
| $F^-$ | 1.54 | 0.36 | 5.97 | 0.2-5 | 0.992 | 0.005 |
| $CH_3SO_3^-$ | 1.67 | 0.43 | 4.73 | 0.2-5 | 0.996 | 0.033 |
| $PO_4^{3-}$ | 2.41 | 0.74 | 3.71 | 0.5-10 | 0.996 | 0.061 |

4.2. Flow Injection Coupled Autonomous Analysis

Figure 6:
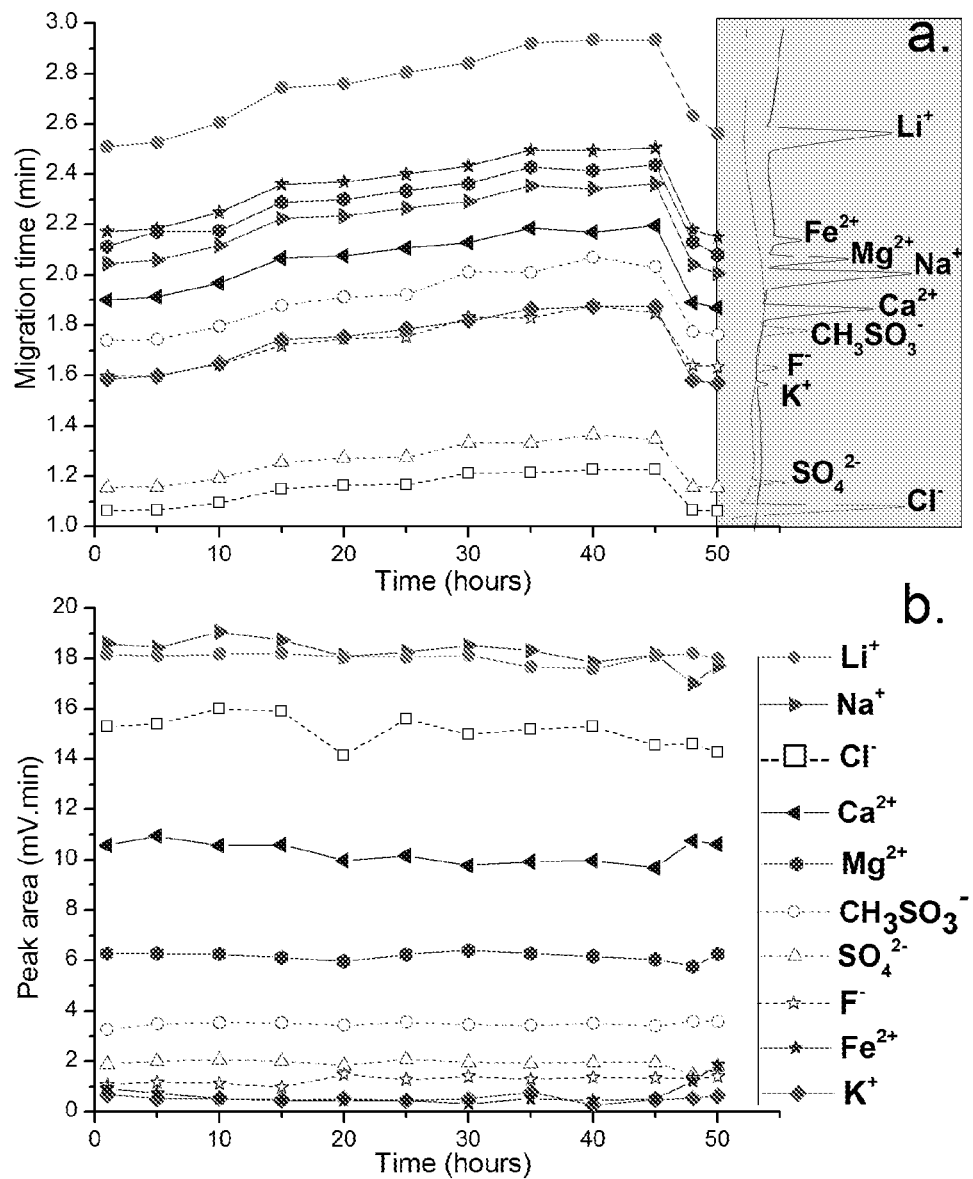
FIG. 6(a) is a graph showing the reproducibility of migration times (min) of tap water analytes over a continuous 50 hour period.
FIG. 6(b) is a graph showing the reproducibility of peak areas (mv. Min) of tap water analytes over a continuous 50 hours period. $Li^+$ and $CH_3SO_3^-$ are cation and anion IS respectively. A representative electropherogram of the separation at T≈50 h at the right of (a).

Using the system setup described in FIG. 1($b$), a two day online analysis of tap water was conducted in the laboratory. This consisted of 900 consecutive runs of 3.5 minutes per run (approximately 17 runs per hour) where samples were aspirated from a running reservoir of tap water to the quaternary pump, with FIG. 6 showing the results from one separation every 5 hours over this period. Internal Standard (200 ppm MSA, 100 ppm $Li^+$) was drawn from a reservoir via a second pump inlet line. The sample and IS were mixed at a flow rate ratio of 0.1 mL/min IS:0.9 mL/min sample. This resulted in a 10% dilution of the sample and provided IS concentrations of 5 mg/mL for $Li^+$ and 10 mg/mL for MSA. The sample/IS outlet line was plumbed directly to the sample injection port. The experiment occurred over a weekend period during winter and commenced at 0930 am on a Saturday morning. Internal heating to the building was turned off over the period covering 4 μm the preceding Friday through to 0800 am the following Monday. Significant variations in migration times seen in FIG. 6($a$) are due to the change in temperature over the period of the experiment. These variations in migration times appear to have negligible effect on the variation of IS peak areas as shown in FIG. 6($b$) (% RSD<3% for both standards calculated from the 12 sampled values) over the period examined FIG. 6 ($b$). These results indicate that variations seen in analyte peak areas are a result of real variation and not due to system error. Indeed, the final two data points show a significant percentage increase in $Fe^{2+}$ peak area as work resumed on Monday morning and people begin to use water throughout the building, increasing the concentration of $Fe^{2+}$ moving through the plumbing. The system was not rigorously examined with regards to quantification. With further consideration given to thermal insulation of the system and the development of automated data processing software, these results indicate a stable, reproducible system that may be readily adapted to a number of autonomous applications.

Conclusions

In this example we have demonstrated the effectiveness of this new method for the simultaneous separation of anions and cations by CE from a single injection point. Whilst the use of a single BGE for the separation of both cations and anions remains a drawback, the ability to vary individual capillary wall coatings and detector distances simplifies optimisation of the separation of both anions and cations far easier than can be performed with dual-opposite end injection CE. The system is suitable for a range of applications and is capable of simultaneously separating at least 11 anions and 12 cations within a total analysis time of 3.5 min. The ability to sample directly online make this a potentially useful system for the simultaneous analysis of cations and anions in both laboratory and extended automated monitoring applications as demonstrated for the analysis of tap water samples in the laboratory on-line over a period of 48 hours. Any drawbacks associated with the use of a single background electrolyte are overcome in the following example.

Example 2

In this example a microfluidic approach was used for delivering individualised separation chemistries (background electrolyte compositions) to separate microchannels for simultaneous analysis of the analytes in a sample. In addition to electrokinetic injection, a new method was developed for hydrodynamic injection of a single sample into two separation channels using dyes and applied to the analysis of inorganic cations. The technique used involved (i) laminar flow to introduce flexible and individual separation chemistries with optimal selectivity for simultaneous comprehensive analysis and (ii) hydrodynamic control for non-biased injections in chip CE.

1. Experimental

In microfluidic channels, a low Reynolds number dictates a laminar flow regime. Laminar flow enables different liquids to flow alongside one and another without mixing other than by diffusion.

Figure 10:
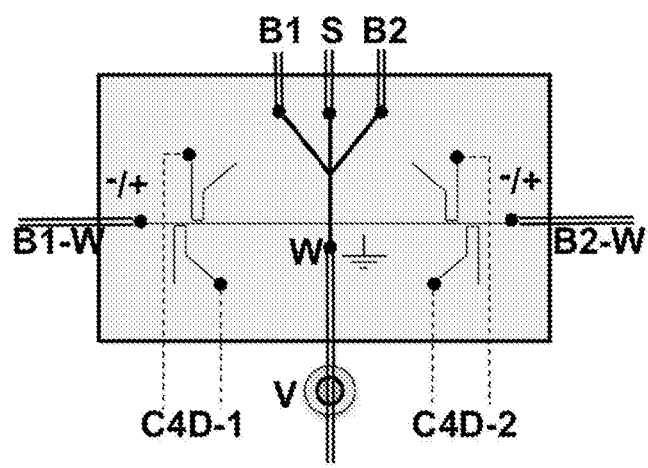
FIG. 10 is a schematic diagram showing the microchip electrophoresis system, or device, for delivering different background electrolyte (or buffer) chemistries to each of two separation channels, used in one Example. Inlets S, B1 and B2 refer to the inlets of sample, buffer 1 and buffer 2, respectively, and are connected with external pumps. Outlets W, B1-W and B2-W correspond to the waste and the ends of the separation channels filled with B1 and B2, respectively and connected to HV electrodes; W is also connected to isolation valve V. Channels B1-W and B2-W are equipped with an integrated contactless conductivity detector.

The chip design used for the flow experiments is shown in FIG. 10. Channel structures (height 15 μm) were made by hot embossing in 1.5 mm PMMA using a PDMS master, and were sealed with a 1.5 mm thick PMMA substrate using an office laminator. Channels S, B1 and B2 are 450 μm wide; channels B1-W and B2-W 50 μm wide. PMMA ports with tapped treads were attached to the reservoirs to enable fluidic interfacing using standard Upchurch fittings. Sample and the two BGE's, B1 and B2, were pumped into the device using MilliGAT pumps, and flow could be directed into B1-W and B2-W by closing an isolation valve at W. HV electrodes were interfaced with the Upchurch fittings.

A new method was developed for the integration of electrodes for capacitively coupled contactless conductivity detection (C4D) by filling microchannels with a molten metal alloy. Briefly, the PMMA devices were heated to 80° C. following bonding. Wood's metal, a low metal point alloy, was positioned above a reservoir and drawn into the microchannel using vacuum. The chip was allowed to cool down to room temperature, solidifying the electrode. The detection electrodes were connected to the chip head of a TraceDEC detector and used for C4D. Data acquisition, and control of the pumps, valve and HV supplies was controlled using NI Labview.

2. Results and Discussion

The chip design comprised three inlets for S, B1 and B2, respectively, each connected with a milliGAT pump. When the valve V was open, the flow left the chip at W. Flow into the 50 μm wide channels B1-W and B2-W was restricted by their high hydrodynamic resistance. When valve V was closed, the increased pressure forced liquid into channel B1-W and B2-W, a phenomena used to fill these channels with BGE, and to inject a small plug of sample.

To study the new injection protocol, food dyes were used to visualise BGE 1 (B1, yellow); sample (S, red) and BGE 2 (B2, blue). When pumping B1 and B2 through the chip, closing the isolation valve forced B1 and B2 into channels B1-W and B2-W, respectively. Sample was then introduced into the chip from S only, and a small plug entered both separation channels during a brief closure of valve V (pumps B1 and B2 were off). After re-opening V and resuming flows B1 and B2, the sample plug remained captured in channels B1-W and B2-W, respectively. This was evident from visual observation of a red sample plug section with yellow BGE in front of and behind the sample plug in one of the separation channels, and another red sample plug section with blue BGE in front of and behind the sample plug in the second of the separation channels. Switching on the HV power supplies initiated the separation towards B1-W and B2-W.

The molten metal electrodes prepared by the technique described above were used as C4D detection electrodes and metal pins were used for connection with external detection electronics. The continuity of the electrodes was confirmed by connecting it in a circuit with a LED.

Figure 11A:
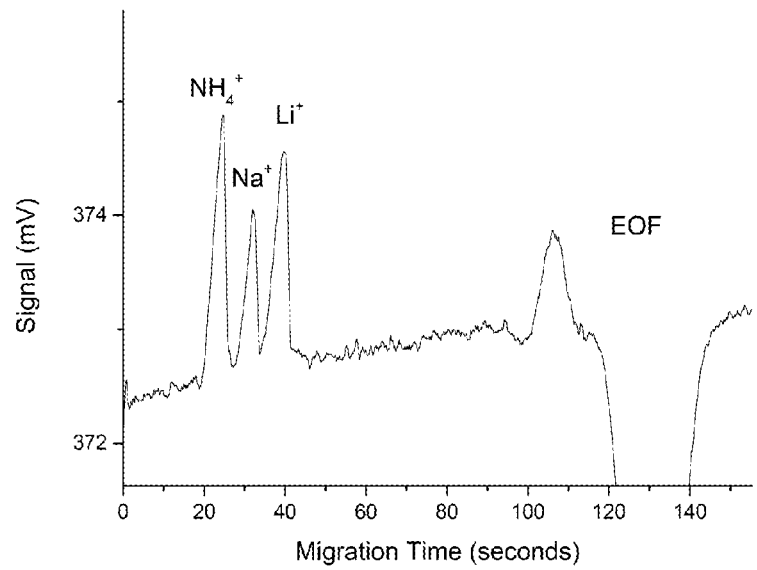
FIG. 11 shows electropherograms following (a) hydrodynamic injection and (b) electrokinetic injection of 5 ppm ammonium, sodium and lithium ions separated at 4500V over a 90 mm channel. The first BGE is 50 mM acetic acid and the second BGE is 10 mM histidine.
Figure 11B:
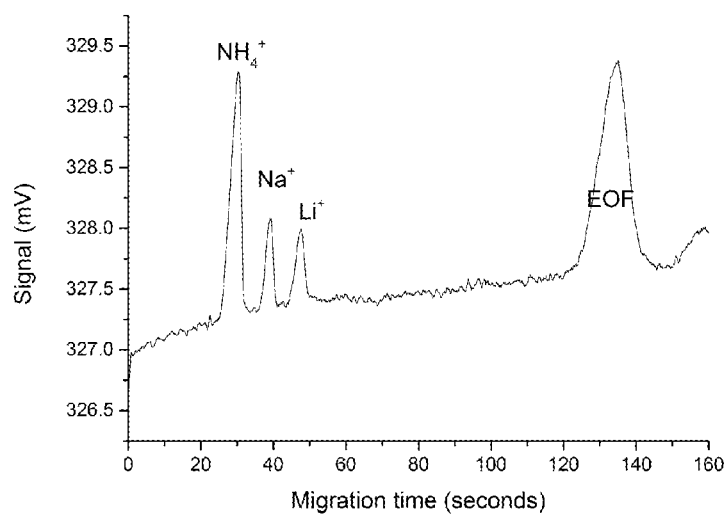

The design depicted in FIG. 10 was modified, extending the separation channels to 90 mm. The footprint of the substrate (5×7.5 cm) remained unchanged, and the separation channels were curved to fit these dimensions. The integrated electrodes for C4D were positioned at 70 mm from the injection point. Because the electrode channels are defined lithographically together with the separation channels, no further alignment is required. FIG. 11(a) shows an electropherogram of the separation of 5 ppm ammonium, sodium and lithium following hydrodynamic injection. To demonstrate the versatility of the flow-control system, it was also applied for electrokinetic detection. Under these conditions, channels B1-W and B2-W were filled with BGE as explained above. Sample was introduced into the chip from S only (pumps B1 and B2 were off), and application of potentials to electrodes B1-W and B2-W injected a small sample zone into the separation channels. FIG. 11(b) gives the electropherogram obtained following electrokinetic injection in the flow-through chip. The separation efficiency and resolution obtained following electrokinetic injection are slightly higher than following hydrodynamic injection. More importantly, the sensitivity during both the hydrodynamic and electrokinetic injections is higher than achieved in devices with the same detector geometry using pinched injection in a standard cross device.

This example demonstrates the efficacy of a flow-through microchip using laminar flow for simultaneous complementary electrophoretic analysis with individualised separation chemistries. The fluidic control enables a new way to hydrodynamically inject a small (60 μm long) sample plug into two separate separation channels, eliminating electrophoretic bias. Molten metal electrodes were used for conductivity detection following hydrodynamic and electrokinetic injection using the new, flow-through device, with electrokinetic injection achieving higher resolution and efficiency.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for the simultaneous separation and detection of analytes in a sample through two or more separation channels using electrophoresis, the method comprising:
   injecting a sample into an electrophoresis system comprising a fluid channel having a fluid channel inlet at one end and a fluid channel outlet at the opposite end, wherein the fluid channel inlet is in fluid communication with a single sample injection port, and wherein an interface zone is positioned between the fluid channel inlet and the fluid channel outlet, two or more separation channels with entrances positioned in the interface zone of the fluid channel, and a ground electrode located in the interface zone between the entrances to the two separation channels, wherein the sample is injected through the single sample injection port which is in fluid communication with the two separation channels;
   separating analytes in each of the separation channels; and
   detecting the analytes separated in each of the separation channels.

2. The method of claim 1, wherein the analytes comprise anions and cations, wherein separating analytes in each of the separation channels and detecting the analytes separated in each of the separation channels comprises:

separating the cations in a first of the two separation channels and the anions in a second of the two separation channels; and
detecting the cations in the first separation channel and the anions in the second separation channel.

3. The method of claim 2, further comprising:
applying a positive potential across the first of the separation channels; and
applying a negative potential across the second of the separation channels.

4. The method of claim 2, further comprising hydrodynamically loading the sample into the two separation channels prior to separating the cations and the anions simultaneously in their respective separation channels.

5. The method of claim 4, wherein the hydrodynamic loading comprises controlled opening and closing a valve associated with said fluid channel.

6. The method of claim 5, wherein hydrodynamically loading the sample comprises:
priming the separation channels by closing the fluid channel outlet valve to hydrodynamically force the background electrolyte into the first and second separation channels;
loading the sample into the interface zone of the fluid channel with the fluid channel outlet open;
closing the fluid channel outlet and injecting the sample through the sample injection port to hydrodynamically force the sample into the two separation channels to load the sample into the separation channels;
introducing background electrolyte through the fluid channel and into the interface zone of the fluid channel with the fluid channel outlet open; and
applying a voltage potential across the separation channels to effect separation of the analytes during flow of background electrolyte through the fluid channel.

7. The method of claim 2, further comprising electrokinetically loading the sample into the two separation channels prior to effecting the separation of cations and anions simultaneously in the respective separation channels.

8. The method of claim 7, wherein the electrokinetic loading of the sample comprises applying a voltage potential of between 0.2 kV to 5 kV for between 0.2 and 3 seconds across the two separation channels with a negative voltage applied across the first separation channel, and a positive voltage applied across the second separation channel.

9. The method of claim 1, further comprising channelling two different background electrolytes through each of the separation channels during the separation of cations in one separation channel and anions in the second separation channel.

10. An electrophoresis system for the simultaneous separation and detection of analytes in a sample, the system comprising:
an injection system comprising a single sample injection port;
a fluid channel having a fluid channel inlet at one end and a fluid channel outlet at the opposite end, wherein the fluid channel inlet is in fluid communication with the sample injection port, and wherein an interface zone is positioned between the fluid channel inlet and the fluid channel outlet;
a background electrolyte reservoir for storing background electrolyte, in fluid communication with the injection system to enable flow of the background electrolyte through the fluid channel;
a first separation channel having an entrance positioned in the interface zone of the fluid channel and a first separation channel outlet at an opposite end of the first separation channel;
a second separation channel having an entrance positioned in the interface zone of the fluid channel and a second separation channel outlet at the opposite end at an opposite end of the second separation channel;
a grounded electrode positioned in the fluid channel;
a first charged electrode positioned to apply a potential across the first separation channel;
a first detector positioned to detect analytes passing through a detection zone of the first separation channel;
a second charged electrode positioned to apply a potential across the second separation channel;
a second detector positioned to detect analytes passing through a detection zone of the second separation channel; and
a controller for controlling the injection system, flow of background electrolyte through the fluid channel and the application of a voltage across the electrodes.

11. The system of claim 10, wherein the analytes comprise anions and cations, wherein the first charged electrode is a positively charged electrode, wherein the second charged electrode is a negatively charged electrode, wherein the first detector detects anions and wherein the second detector detects cations.

12. The system of claim 10, wherein the grounded electrode is located in the interface zone between the entrances to the two separation channels.

13. The system of claim 10, wherein the grounded electrode is cylindrical.

14. The system of claim 10, wherein the grounded electrode extends axially from the outlet end of the fluid channel and into the interface zone of the fluid channel.

15. The system of claim 10, wherein:
the background electrolyte reservoir comprises a first background electrolyte reservoir and a second background electrolyte reservoir, with respective injection ports positioned so that background electrolyte injected through the respective injection ports will flow concurrently through portions of the fluid channel to pass through portions of the interface zone of the fluid channel,
the entrance to the first separation channel is positioned in the portion of the interface zone through which the stream of background electrolyte from the first background electrolyte injection port will pass, and
the entrance to the second separation channel is positioned in the portion of the interface zone through which the stream of background electrolyte from the second background electrolyte injection port will pass.

16. The system of claim 10, wherein the grounded electrode is positioned in the interface zone of the fluid channel.

17. A method for the separation and detection of analytes in a sample using electrophoresis in the presence of two or more different electrolytes concurrently, the method comprising:
providing an electrophoresis system comprising a single sample injection port in fluid communication with two or more separation channels;
priming the separation channels with different background electrolytes;
injecting the sample through the single sample injection port and into each of the separation channels;
applying a voltage potential across each of the separation channels to effect a separation of the analytes in the respective channels during the flow of a different background electrolyte composition through each of the separation channels; and detecting the presence of the analytes in the sample.

18. The method of claim 17, wherein the electrophoresis system comprises:
  a fluid channel having a fluid channel inlet at one end and a fluid channel outlet at an opposite end,
  wherein the fluid channel inlet is in fluid communication with the sample injection port, a first background electrolyte injection port and a second background electrolyte injection port, and
  wherein an interface zone of the fluid channel is positioned between the fluid channel inlet and the fluid channel outlet, with inlets to the two respective separation channels opening into portions of the interface zone, and
  wherein the method comprises injecting said different background electrolytes through the first and second background electrolyte ports respectively to flow concurrently through said portions of the interface zone of the fluid channel.

19. The method of claim 18, further comprising hydrodynamically loading the sample into the two separation channels prior to effecting the separation of analytes simultaneously in the respective separation channels.

20. The method of claim 19, wherein the hydrodynamic loading of sample comprises:
  priming the two separation channels by closing the fluid channel outlet valve and hydrodynamically forcing background electrolyte from the first and second background electrolyte injection ports into the first and second separation channels;
  loading of sample into interface zone the fluid channel outlet open;
  closing the fluid channel outlet and injecting the sample through the sample injection port to hydrodynamically force the sample into the two separation channels to load the sample into the separation channels;
  introducing different background electrolytes through the fluid channel and into portions of the interface zone of the fluid channel with the fluid channel outlet open; and
  applying a voltage potential across the separation channels to effect separation of the analytes during flow of different background electrolyte through portions of the interface zone of the fluid channel.

21. The method of claim 17, wherein the analytes are anions and cations, and wherein the cations are separated in a first of the two separation channels, and the anions are separated in a second of the two separation channels.

* * * * *